US010953040B2

(12) United States Patent
Rice

(10) Patent No.: US 10,953,040 B2
(45) Date of Patent: Mar. 23, 2021

(54) METHODS OF TREATING BACTERIAL INFECTIONS WITH PENAM β-LACTAM ANTIBIOTICS AND BRANCHED POLY(ETHYLENIMINE)

(71) Applicant: THE BOARD OF REGENTS OF THE UNIVERSITY OF OKLAHOMA, Norman, OK (US)

(72) Inventor: Charles V. Rice, Norman, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 0 days.

(21) Appl. No.: 16/530,756

(22) Filed: Aug. 2, 2019

(65) Prior Publication Data

US 2019/0358256 A1    Nov. 28, 2019

Related U.S. Application Data

(63) Continuation of application No. 15/736,675, filed as application No. PCT/US2016/037799 on Jun. 16, 2016, now abandoned.

(60) Provisional application No. 62/180,976, filed on Jun. 17, 2015.

(51) Int. Cl.
| | | |
|---|---|---|
| A61K 31/546 | (2006.01) | |
| A61K 31/545 | (2006.01) | |
| A61K 31/04 | (2006.01) | |
| A61K 31/43 | (2006.01) | |
| A61K 31/785 | (2006.01) | |
| A61P 31/04 | (2006.01) | |

(52) U.S. Cl.
CPC ............ *A61K 31/785* (2013.01); *A61K 31/43* (2013.01); *A61K 31/545* (2013.01); *A61K 31/546* (2013.01); *A61P 31/04* (2018.01); *Y02A 50/30* (2018.01)

(58) Field of Classification Search
CPC .... A61K 31/43; A61K 31/545; A61K 31/546; A61P 31/04; Y02A 50/30
See application file for complete search history.

(56) References Cited

U.S. PATENT DOCUMENTS

| | | | |
|---|---|---|---|
| 2010/0311770 A1 | 12/2010 | Kirschner et al. | |
| 2011/0044968 A1 | 2/2011 | Bolotin et al. | |
| 2012/0190632 A1* | 7/2012 | Chen ...................... | A61P 31/04 514/25 |

OTHER PUBLICATIONS

Wiegand et al. (International Journal of Pharmaceutics, 456, 2012, 165-174.*
Hansen, M.B., et al.; "Re-examination and further development of a precise and rapid dye method for measuring cell growth / cell kill"; Journal of Immunological Methods; 119 (1989) 203-210.

(Continued)

*Primary Examiner* — Anna Pagonakis
(74) *Attorney, Agent, or Firm* — Hall Estill Law Firm

(57) ABSTRACT

The present disclosure describes compositions comprising β-lactam antibiotics and branched polyethylenimines (BPEI), having efficacy against various Gram-positive bacteria, for example Gram-positive bacteria having resistance against β-lactam antibiotics, one non-limiting example of which is Methicillin-resistant *Staphylococcus aureus* (MRSA). The compositions result in the resensitization of such resistant bacterial strains to traditional antibiotic therapies such as β-lactam antibiotics.

15 Claims, 22 Drawing Sheets

(56) References Cited

OTHER PUBLICATIONS

Helander, I.M., et al.; "Polyethyleneimine is an effective permeabilizer of Gram-negative bacteria"; Microbiology 143 (1997) 3193-3199.
Bhavsar, A.P., et al.; "Teichoic Acid Is an Essential Polymer in Bacillus subtilis That is Functionally Distinct from Teichuronic Acid"; Journal of Bacteriology; 186:23 (Dec. 2004) 7865-7873.
D'Elia, M.A., et al.; "Wall Teichoic Acid Polymers Are Dispensable for Cell Viability in Bacillus subtilis"; Journal of Bacteriology; 188:23 (Dec. 2006) 8313-8316.
Khalil, H., et al.; "Synergy between Polyethylenimine and Different Families of Antibiotics against a Resistant Clinical Isolate of Pseudomonas aeruginosa"; Antimicrobial Agents and Chemotherapy; 52:5 (May 2008) 1635-1641 (published ahead of print on Feb. 19, 2008).
Wickham, J.R., et al.; "Revisting Magnesium Chelation by Teichoic Acid with Phosphorus Solid-State NMR and Theoretical Calculations"; J. Phys. Chem. B; 113:7 (2009) 2177-2183.
Swoboda, J.G., et al.; "Discovery of a Small Molecule that Blocks Wall Teichoic Acid Biosynthesis in *Staphylococcus aureus*"; ACS Chemical Biology; 4:10 (Aug. 18, 2009) 875-883.
Halye, J.L., et al.; "Cadmium Chelation by Bacterial Teichoic Acid from Solid-State Nuclear Magnetic Resonance Spectroscopy"; Biomacromolecules; 11 (2010) 333-340 (published on Web Jan. 13, 2010).
Campbell, J.; et al.; "Synthetic Lethal Compound Combinations Reveal a Fundamental Connection between Wall Teichoic Acid and Peptidoglycan Biosynthesis in *Staphylococcus aureus*"; ACS Chemical Biology; 6:1 (Oct. 20, 2010) 106-116.
Gibney, K., et al.; "Poly(ethylene imine)s as antimicrobial agents with selective activity"; Macromol. Biosci.; (2012) 22 pages.
Gibney, K.A, et al.; "Poly(ethylene imine)s as Antimicrobial Agents with Selective Activity"; Macromol. Biosci.; 12 (2012) 1279-1289.
Farha, M.A., et al.; "Inhibition of WTA Synthesis Blocks the Cooperative Action of PBPs and Sensitizes MRSA to B-Lactams"; ACS Chem. Biol.; 8 (2013) 226-233 (Published on Oct. 14, 2012).
Roemer, T.; et al.; "Auxilliary factors: a chink in the armor of MRSA resistance to B-lactam antibiotics"; Current Opinion in Microbiology; 16 (2013) 538-548.
Wang, H., et al.; "Discovery of Wall Teichoic Acid Inhibitors as Potential Anti-MRSA B-Lactam Combination Agents"; Chemistry & Biology; 20 (Feb. 21, 2013) 272-284.
Thomas, III, K.J., et al.; "Revised model of calcium and magnesium binding to the bacterial cell wall"; Biometals; 27 (2014) 1361-1370.
Foxley, M.A., et al.; "Efficacy of ampicillin against methicillin-resistant *Staphylococcus aureus* restored through synergy with branched poly(ethylenimine)"; The Journal of Antibiotics (May 18, 2016) 1-8.
PCT/US2016/037799; International Search Report and Written Opinion; dated Sep. 9, 2019; 22 pages.
Office Action; U.S. Appl. No. 15/736,675; dated Sep. 19, 2018; 13 pages.
Response to Office Action; U.S. Appl. No. 15/736,675, filed Dec. 21, 2018; 14 pages.
Corrected Response to Office Action; U.S. Appl. No. 15/736,675, filed Mar. 7, 2019; 4 pages.
Final Office Action; U.S. Appl. No. 15/736,675; dated May 3, 2019; 10 pages.
"Methicillin-Resistant and Methicillin-Sensitive Research Materials"; ATCC; Methicillin-Resistant *Staphylococcus* (MRS) Research Material (2010) 4 pages.
Wiegand, C., et al.; "Poly(ethyleneimines) in dermal applications: Biocompatibility and antimicrobial effects"; International Journal Journal of Pharmaceutics (2013) 456:165-174.
Johns Hopkins ABX Guide; "*Staphylococcus aureus*"; (2020) 19 pages.
Miller, B.W., et al.; "Synergistic anti-methicillin-resistant *Staphylococcus aureus* (MRSA) activity and absolute stereochemistry of 7,8-dideoxygriseorhodin C"; The Journal of Antibiotics (2020) 73:290-298.

\* cited by examiner

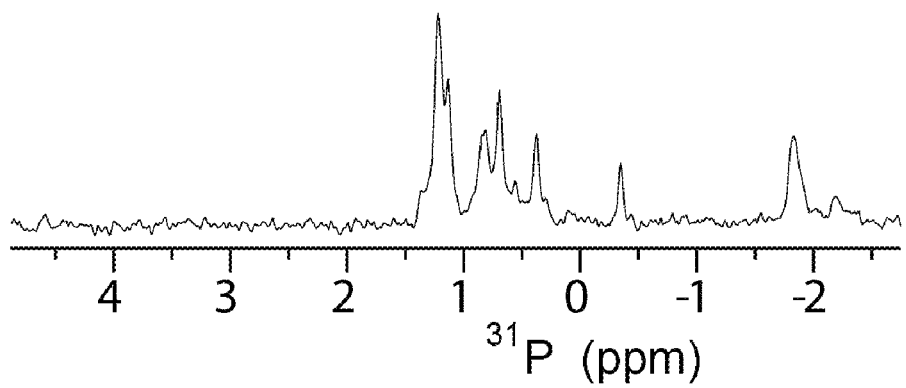
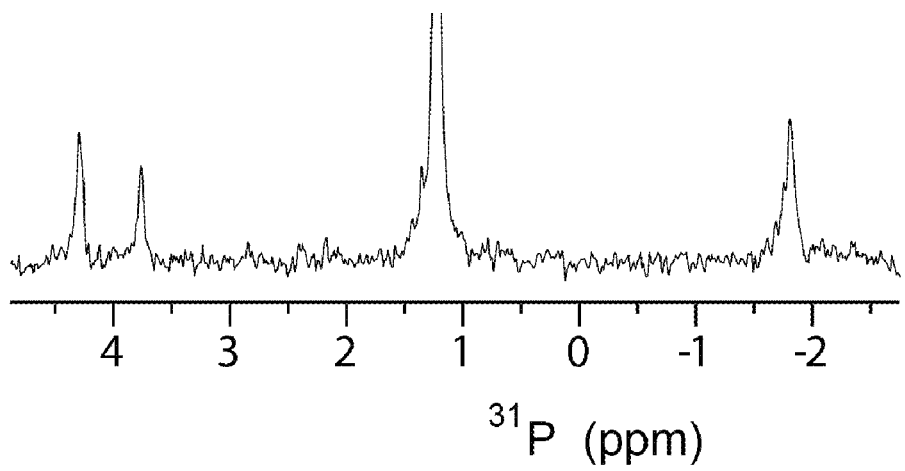
FIG. 17A-B

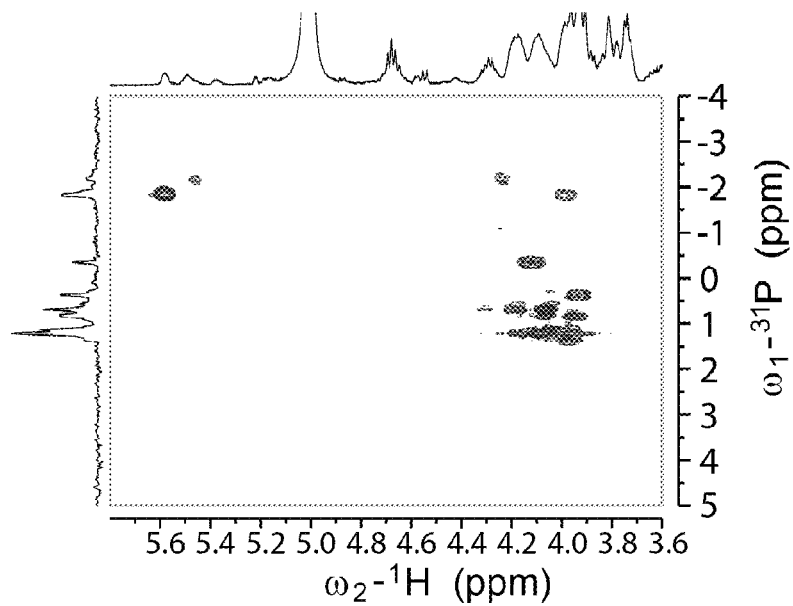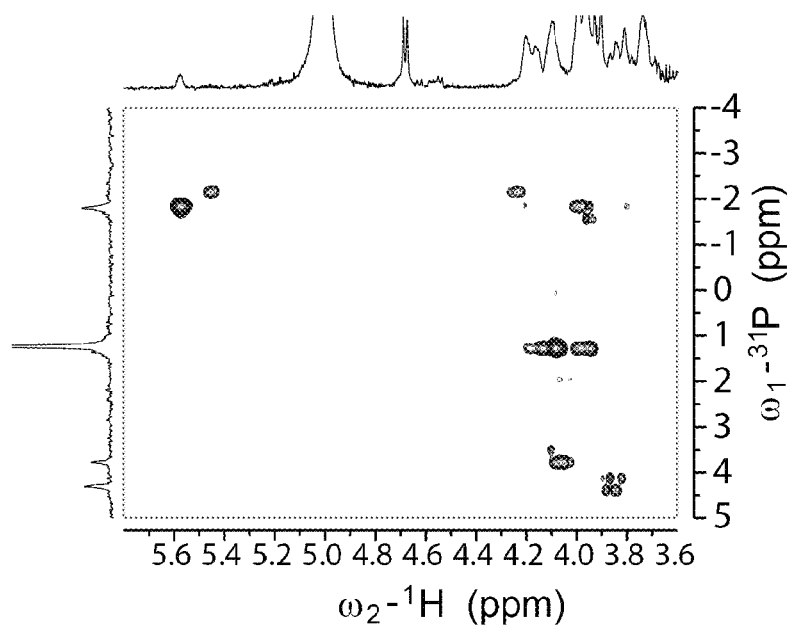
FIG. 17C-D

METHODS OF TREATING BACTERIAL INFECTIONS WITH PENAM β-LACTAM ANTIBIOTICS AND BRANCHED POLY(ETHYLENIMINE)

CROSS-REFERENCE TO RELATED APPLICATIONS

The present application is a continuation application of U.S. Ser. No. 15/736,675, filed Dec. 14, 2017, which is a national stage application of a PCT application having International Application No. PCT/US2016/037799, filed Jun. 16, 2016, which claims benefit under 35 U.S.C. § 119(e) of U.S. Provisional Patent Application Ser. No. 62/180,976 entitled "ANTIBIOTIC COMPOSITIONS AND METHODS OF USE" filed on Jun. 17, 2015, the entire contents of each of the above-referenced applications are hereby expressly incorporated herein by reference.

STATEMENT REGARDING FEDERALLY SPONSORED RESEARCH OR DEVELOPMENT

This invention was made with government support under Grant No. 1R01GM090064-01 awarded by the National Institutes of Health (NIH) and National Institute of General Medical Science (NIGMS). The government has certain rights in the invention.

BACKGROUND

Resistance of certain bacterial strains to previously-effective antibiotics is a growing global problem. For example, colonies of methicillin-resistant *Staphylococcus aureus* (MRSA) bacteria invade host tissue to release toxins that cause tissue injury, leading to significant patient morbidity. The patient suffers while numerous first- and second-line antibiotics are prescribed to no avail. This increases the threat of MRSA to public health. Timely MRSA diagnosis and delivering drugs of last resort are essential to prevent mortality. In 2011 for example, MRSA infected 80,500 people and nearly 1 in 7 cases resulted in death (11,300; 14%). While, several antibiotics of last resort (vancomycin, linezolid, daptomycin) are effective at killing MRSA, and there has never been a *S. aureus* isolate resistant to all approved antibiotics, patients still die from MRSA infections. The reason for this is because the drugs of last resort are given after morbidity from staphylococcal toxins has set in, too late to prevent mortality. Moreover, vancomycin, a primary treatment option after MRSA diagnosis, presents additional barriers of high cost and toxicity. New antibiotics, such as oxadiazoles, tedizolid, and teixobactin, are awaiting FDA approval to meet the critical need for new treatments because *S. aureus* strains resistant to vancomycin and β-lactams have emerged. New treatment options for MRSA and other bacterial strains which have become resistant to standard β-lactam antibiotics are needed.

Originally acquired exclusively in health care settings, MRSA is now regularly found outside the health care environment for a variety of reasons including drug-resistance, which hinders efforts to develop safe clinical treatments for MRSA infections. Resistance mechanisms include a novel penicillin-binding protein 2a (PBP2a) with a lower affinity for β-lactams than the native penicillin-binding protein 2 (PBP2) protein. β-lactamases, enzymes that degrade β-lactam antibiotics, are also common. Approaches to overcome these resistance factors are efflux-pump inhibitors that increase the intracellular concentration of antibiotics, using β-lactamase inhibitors, or increasing cell wall permeability. Nevertheless, the cell wall remains an especially rich antimicrobial target, containing many components shown to contribute to resistance, such as excess peptidoglycan, techoic acids and novel proteins. While these approaches have shown promise, the presence of side-effects and slow transfer from discovery to clinical usage have failed to stem the rate of MRSA infection and mortality. Community-acquired MRSA is less likely than healthcare-associated MRSA to exhibit multidrug resistance, but resistance to β-lactam antibiotics is a defining characteristic in both cases. New formulations to effectively treat MRSA and other antibiotic-resistant bacteria are urgently needed.

BRIEF DESCRIPTION OF THE DRAWINGS

Several embodiments of the present disclosure are hereby illustrated in the appended drawings. It is to be noted however, that the appended drawings only illustrate several embodiments and are therefore not intended to be considered limiting of the scope of the present disclosure.

FIG. 17A-B shows $^{31}P$ NMR spectra of WTA before (A) and after (B) the addition of low-$M_w$ BPEI demonstrating significant changes in phosphate chemical shift caused by changes in the chemical environment. The P-31 signals near 4 ppm are correlated with the proton signals of NAG sugar groups. However, clear identification of specific interactions is prevented by the heterogeneous nature of WTA functional groups, BPEI branching, and WTA:BPEI binding interactions.

FIG. 17C-D shows $^1H/^{31}P$ heteronuclear multiple-bond correlation (HMBC) NMR spectra of WTA before (C) and after (D) the addition of low-$M_w$ BPEI demonstrating significant changes in phosphate chemical shift caused by changes in the chemical environment.

DETAILED DESCRIPTION

Figure 1:
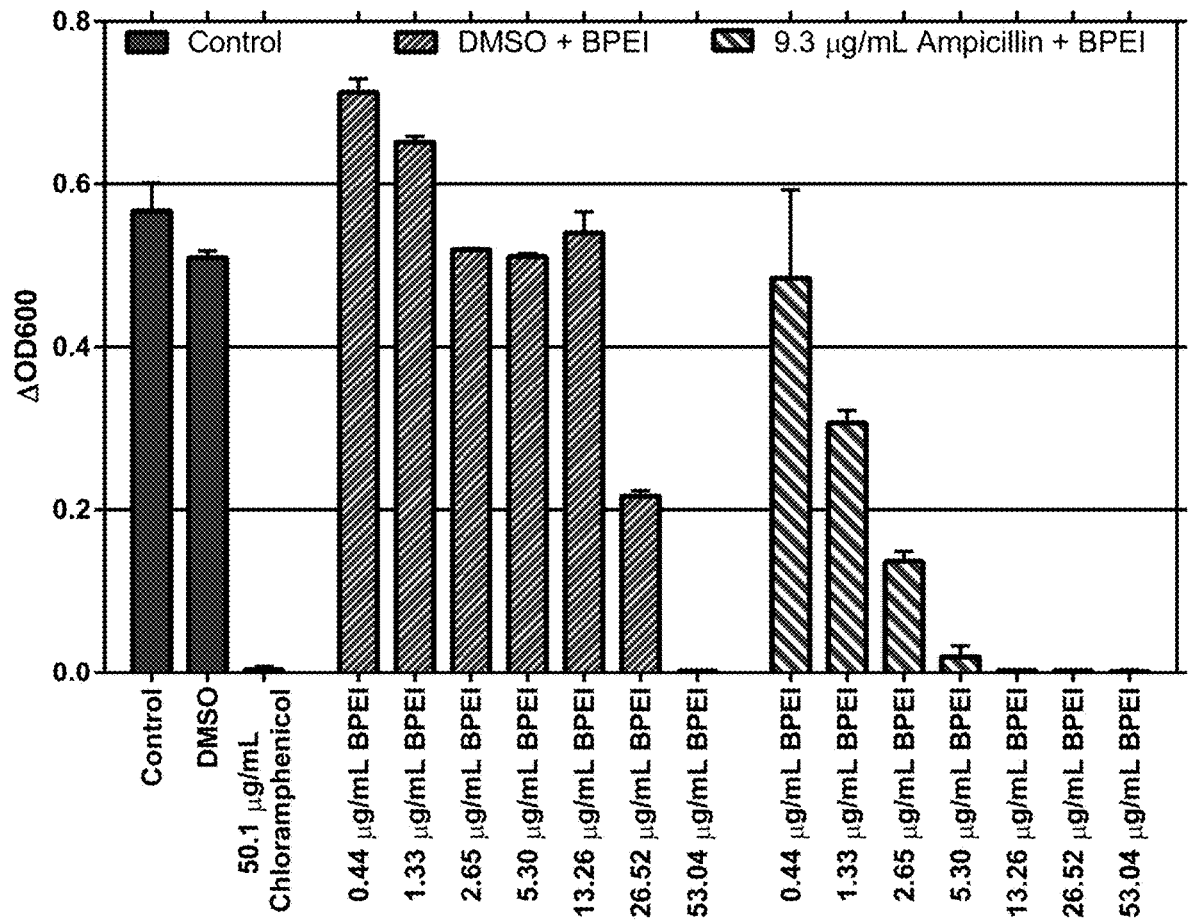
FIG. 1 shows results of an in vitro antimicrobial assay of the effectiveness of BPEI in restoring ampicillin efficacy against MRSA. When the concentration of added ampicillin is constant (9.3 µg/mL), cell growth is not observed when the BPEI concentration is 5.3 µg/mL (right data set, columns with thick diagonal lines). When the BPEI is used without ampicillin, 53 µg/mL of BPEI is required to inhibit cell growth (middle data set, columns with thin diagonal lines). The growth of MRSA was evaluated by measuring the change in $OD_{600}$ after 20 hours. Cell growth in TSB media (control) or media with 1% DMSO are shown by the $\Delta OD_{600}$, with 50 µg/mL chloramphenicol as a negative control.

In at least certain embodiments, the present disclosure is directed to novel compositions comprising antibiotics against which certain bacteria (e.g., Methicillin-resistant *Staphylococcus aureus* (MRSA)) strains have previously been resistant. In other words, the bacterial strains have become resensitized to these novel antibiotic formulations which comprise historical antibiotics, such as, but not limited to, the β-lactams, for example, methicillin, amoxicillin, and ampicillin, and others described elsewhere herein. In particular, results provided herein show that the lost anti-MRSA effectiveness of certain FDA-approved antibiotics, such as ampicillin (or other antibiotic listed elsewhere herein), can be restored via a synergistic effect when they are administered in the presence of branched poly(ethylenimine) (BPEI), a cationic polyamine. Further, the effective levels (i.e., the minimum inhibitory concentration (MIC)) of certain other antibiotics can be substantially reduced (e.g., by about ten-fold) when administered with BPEI.

Before further describing various embodiments of the compositions and methods of the present disclosure in more detail by way of exemplary description, examples, and results, it is to be understood that the present disclosure is not limited in application to the details of methods and compositions as set forth in the following description. The description provided herein is intended for purposes of illustration only and is not intended to be construed in a limiting sense. The inventive concepts of the present disclosure are capable of other embodiments or of being practiced or carried out in various ways. As such, the language used herein is intended to be given the broadest possible scope and meaning; and the embodiments are meant to be exemplary, not exhaustive. Also, it is to be understood that the phraseology and terminology employed herein is for the purpose of description and should not be regarded as limiting unless otherwise indicated as so. Moreover, in the following detailed description, numerous specific details are set forth in order to provide a more thorough understanding of the disclosure. However, it will be apparent to a person having ordinary skill in the art that the present disclosure may be practiced without these specific details. In other instances, features which are well known to persons of ordinary skill in the art have not been described in detail to avoid unnecessary complication of the description. It is intended that all alternatives, substitutions, modifications and equivalents apparent to those having ordinary skill in the art are included within the scope of the present disclosure as defined herein. All of the compositions and methods of production and application and use thereof disclosed herein can be made and executed without undue experimentation in light of the present disclosure. Thus, while the compositions and methods of the present disclosure have been described in terms of particular embodiments, it will be apparent to those of skill in the art that variations may be applied to the compositions and/or methods and in the steps or in the sequence of steps of the method described herein without departing from the concept, spirit, and scope of the inventive concepts.

All patents, published patent applications, and non-patent publications mentioned in the specification are indicative of the level of skill of those skilled in the art to which the present disclosure pertains. All patents, published patent applications, and non-patent publications referenced in any portion of this application are herein expressly incorporated by reference in their entirety to the same extent as if each individual patent or publication was specifically and individually indicated to be incorporated by reference.

Unless otherwise defined herein, scientific and technical terms used in connection with the present disclosure shall have the meanings that are commonly understood by those having ordinary skill in the art. Further, unless otherwise required by context, singular terms shall include pluralities and plural terms shall include the singular.

As utilized in accordance with the methods and compositions of the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or when the alternatives are mutually exclusive, although the disclosure supports a definition that refers to only alternatives and "and/or." The use of the term "at least one" will be understood to include one as well as any quantity more than one, including but not limited to, 2, 3, 4, 5, 6, 7, 8, 9, 10, 15, 20, 30, 40, 50, 100, or any integer inclusive therein. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

Throughout this application, the term "about" is used to indicate that a value includes the inherent variation of error for the composition, the method used to administer the composition, or the variation that exists among the study subjects. As used herein the qualifiers "about" or "approximately" are intended to include not only the exact value, amount, degree, orientation, or other qualified characteristic or value, but are intended to include some slight variations due to measuring error, manufacturing tolerances, stress exerted on various parts or components, observer error, wear and tear, and combinations thereof, for example. The term "about" or "approximately", where used herein when referring to a measurable value such as an amount, a temporal duration, and the like, is meant to encompass, for example, variations of ±20% or ±10%, or ±5%, or ±1%, or ±0.1% from the specified value, as such variations are appropriate to perform the disclosed methods and as understood by persons having ordinary skill in the art. As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

The term "pharmaceutically acceptable" refers to compounds and compositions which are suitable for administration to humans and/or animals without undue adverse side effects such as toxicity, irritation and/or allergic response commensurate with a reasonable benefit/risk ratio.

By "biologically active" is meant the ability to modify the physiological system of an organism without reference to how the active agent has its physiological effects.

As used herein, "pure," or "substantially pure" means an object species is the predominant species present (i.e., on a molar basis it is more abundant than any other object species in the composition thereof), and particularly a substantially purified fraction is a composition wherein the object species comprises at least about 50 percent (on a molar basis) of all macromolecular species present. Generally, a substantially pure composition will comprise more than about 80% of all macromolecular species present in the composition, more particularly more than about 85%, more than about 90%, more than about 95%, or more than about 99%. The term "pure" or "substantially pure" also refers to preparations where the object species (e.g., the peptide compound) is at least 60% (w/w) pure, or at least 70% (w/w) pure, or at least 75% (w/w) pure, or at least 80% (w/w) pure, or at least 85% (w/w) pure, or at least 90% (w/w) pure, or at least 92% (w/w) pure, or at least 95% (w/w) pure, or at least 96% (w/w) pure, or at least 97% (w/w) pure, or at least 98% (w/w) pure, or at least 99% (w/w) pure, or 100% (w/w) pure.

The terms "subject" and "patient" are used interchangeably herein and will be understood to refer to a warm blooded animal, particularly a mammal, and more particularly, humans. Animals which fall within the scope of the term "subject" as used herein include, but are not limited to, dogs, cats, rats, mice, guinea pigs, chinchillas, horses, goats, ruminants such as cattle, sheep, swine, poultry such as chickens, geese, ducks, and turkeys, zoo animals, Old and New World monkeys, and non-human primates. Veterinary diseases and conditions which may be treated with the compositions of the presently disclosed inventive concepts include, but are not limited to, anthrax, listeriosis, leptospirosis, clostridial and corynebacterial infections, streptococcal mastitis, and keratoconjunctivitis in ruminants; erysipelas, streptococcal and clostridial infections in swine; tetanus, strangles, streptococcal and clostridial infections, and foal pneumonia in horses; urinary tract infections, and streptococcal and clostridial infections in dogs and cats; and necrotic enteritis, ulcerative enteritis and intestinal spirochetosis in poultry.

"Treatment" refers to therapeutic treatments. "Prevention" refers to prophylactic or preventative treatment measures. The term "treating" refers to administering the composition to a patient for therapeutic purposes.

The terms "therapeutic composition" and "pharmaceutical composition" refer to an active agent-containing composition that may be administered to a subject by any method known in the art or otherwise contemplated herein, wherein administration of the composition brings about a therapeutic effect as described elsewhere herein. In addition, the compositions of the present disclosure may be designed to provide delayed, controlled, extended, and/or sustained release using formulation techniques which are well known in the art.

The term "β-lactam antibiotic" refers to the class of antibiotic agents that have a β-lactam ring or derivatized β-lactam ring in their molecular structures. Examples of such β-lactam antibiotics include but are not limited to, penams, including but not limited to, penicillin, benzathine penicillin, penicillin G, penicillin V, procaine penicillin, ampicillin, amoxicillin, methicillin, cloxacillin, dicloxacillin, flucloxacillin, nafcillin, oxacillin, temocillin, mecillinam, carbenicillin, ticarcillin, and azlocillin, mezlocillin, piperacillin; cephems, including but not limited to, cephalosporin C, cefoxitin, cephalosporin, cephamycin, cephem, cefazolin, cephalexin, cephalothin, cefaclor, cefamandole, cefuroxime, cefotetan, cefoxitin, cefixime, cefotaxime, cefpodoxime, ceftazidime, ceftriaxone, cefepime, cefpirome, and ceftaroline; carbapenems and penems including but not limited to, biapenem, doripenem, ertapenem, earopenem, imipenem, primaxin, meropenem, panipenem, razupenem, tebipenem, and thienamycin; and monobactams including but not limited to, aztreonam, tigemonam, nocardicin A, and tabtoxinine β-lactam.

The terms "effective amount", "antibacterially-effective amount", or "therapeutically-effective amount" refers to an amount of an antibiotic composition (β-lactam antibiotic plus BPEI) which is sufficient to exhibit a detectable therapeutic effect against bacterial growth without excessive adverse side effects (such as toxicity, irritation and allergic response) commensurate with a reasonable benefit/risk ratio when used in the manner as described herein. The effective amount for a patient will depend upon the type of patient, the patient's size and health, the nature and severity of the condition to be treated, the method of administration, the duration of treatment, the nature of concurrent therapy (if any), the specific formulations employed, and the like. Thus, it is not possible to specify an exact effective amount in advance for a given subject or patient. However, the effective amount for a given situation can be determined by one of ordinary skill in the art using routine experimentation based on the information provided herein.

In some embodiments of the present disclosure a low molecular weight ("low Mw") BPEI is used in combination with an anti-bacterial agent to treat and/or inhibit a resistant bacterial infection and/or the growth of resistant bacterial infection, e.g., by sensitizing a bacterium that was previously resistant to an antibacterial agent, are described herein. In certain non-limiting embodiments the low Mw BPEI of the present disclosure has a Mw in range of, for example, 0.1 kDa (kilodaltons) to 25 kDa. Examples of BPEI compounds which may be used in various embodiments of the present disclosure include but are not limited to those shown in U.S. Pat. Nos. 7,238,451 and 9,238,716, and U.S. Published application 2014/0369953, the entireties of which are hereby incorporated by reference herein.

Minimum inhibitory concentration (MIC) of an antibiotic for a particular bacterial strain is defined as the lowest concentration of the antibiotic that is required to inhibit the growth of the bacterium. The MIC is determined by finding the concentration of antibiotic at which there is no growth of the bacterium.

Sensitizing, or sensitization, as the term is used herein, is the process of lowering the MIC of an antibiotic for a resistant bacterial strain to a value that is below the resistance breakpoint for the bacterial strain, thereby causing the bacterium to be more susceptible to that antibiotic.

A breakpoint (or resistance breakpoint) is defined as a concentration of an antibiotic (mg/L) which defines whether a strain of bacteria is susceptible or resistant to the antibiotic. If the MIC is less than or equal to the breakpoint, the strain is considered susceptible to the antibiotic. If the MIC is greater than the breakpoint, the strain is considered intermediate or resistant to the antibiotic.

The compounds and compositions of the present disclosure can be used to treat a subject having resistant bacterial infection, e.g., by administering BPEI in combination with an antibiotic. The combinations of BPEI and the antibacterial agent can result in sensitization of a resistant bacterial strain, e.g., the resistant bacterial strain has a reduced MIC of either the BPEI, or the antibacterial agent, or both, so that the MIC is below the resistance breakpoint for the bacterial strain.

As used herein "resistant bacterial strain" means a bacterial strain which is resistant to an antibacterial agent, e.g. having an MIC that is greater than the resistance breakpoint (as the term is defined herein). In certain embodiments the MIC of a resistant bacterial strain will be at least 2-, 4-, 8-, 10-, 16-, 32-, 64-, or 100-fold greater than for that seen with a non-resistant bacterial strain for a selected antibacterial agent. As used herein, rendering or transforming a resistant bacterial into a sensitive bacterial strain means reducing the MIC, e.g., by at least 2-, 4-, 8-, 10-, 16-, 32-, 64-, or 100-fold.

In some embodiments the combination of the BPEI and the antibiotic results in a reduction in the MIC of the BPEI and/or the antibiotic of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99%, or at least about 99.5%.

The antimicrobial (antibacterial) action of two or more active agents is considered additive if the combined action merely results from the addition of the effects the individual components would have in isolation. In contrast, the antimicrobial action of two or more active compounds is considered to be synergistic if the combined effect of the two or more compounds is stronger than expected based on the assumption of additivity.

More particularly, the term "synergy" or "synergistic" as used herein, refers to an outcome when two agents (e.g., BPEI and an antibiotic) are used in combination, wherein the combination of the agents acts so as to require a smaller amount of each individual agent than would be required of that agent to be efficacious in the absence of the other agent, for example, with lower dosages of the first agent than would be required in the absence of the second agent. In some embodiments, use of synergistic agents can result in the beneficial effect of less overall use of an agent. Typically, evidence of synergistic antimicrobial action may be provided at concentrations below the MICs of each of the components when taken individually. However, a synergistic interaction can also occur when the concentration of one or more of the active compounds is raised above its MIC (when taken individually).

The fractional inhibitory concentration (FIC) as used herein is a measure of the interaction of two agents, such as an antibiotic and a BPEI compound, used together, and is an indicator of synergy. FIC uses a value of the MIC of each of the independent agents, e.g., $MIC_A$ and $MIC_B$ for agents A and B, for a particular bacterium as the basis, then takes the concentration of each component in a mixture where an $MIC_{(A\ in\ B)}$ is observed. For example, for a two component system of agents A and B, $MIC_{(A\ in\ B)}$ is the concentration of A in the compound mixture and $MIC_{(B\ in\ A)}$ is the concentration of B in the compound mixture. The FIC is defined as follows:

$$FIC_A = (MIC_{(A\ in\ B)}/MIC_A) \quad\quad \text{Eqn. 1}$$

$$FIC_B = (MIC_{(B\ in\ A)}/MIC_B) \quad\quad \text{Eqn. 2}$$

$$FIC_{A+B} = FIC_A + FIC_B \quad\quad \text{Eqn. 3}$$

Synergism (i.e., the two compounds together provide a synergistic effect) is defined herein as occurring when $FIC_{A+B} \leq 0.5$. The mixture is defined as having an additive effect when $1 \leq FIC_{A+B} \leq 4$. When, $FIC_{A+B} > 4$ the mixture is considered to have an antagonistic interaction. An example of how FIC is used to determine synergism is shown in U.S. Pat. No. 8,338,476, the entirety of which is incorporated herein by reference in its entirety.

In certain embodiments of the present disclosure, the BPEI/antibiotic combination results in an FIC less than about 0.55, or less than about 0.5, or less than about 0.4, or less than about 0.3, or less than about 0.2, or less than about 0.1, or less than about 0.05, or less than about 0.02, or less than about 0.01, or less than about 0.005, or less than about 0.001. In some embodiments, the combination results in a bactericidal activity at least about 2, at least about 2.5, at least about 3, at least about 3.5, at least about 4, at least about 4.5, or at least about 5 logs more effective than the most effective individual activity, e.g., the activity of the BPEI or the antibiotic agent.

As used herein, "resistant microorganism or bacterium" means an organism which has become resistant to an antibacterial agent. In certain embodiments an MIC of a resistant bacterium will be at least, 2-, 4-, 8-, 10-, 16-, 32-, 64-, or 100-fold greater than that seen with a non-resistant bacterium for a particular anti-bacterial agent. As used herein, the term "resistance breakpoint" is the threshold concentration of an antibacterial agent above which a bacterium is considered resistant, as defined above.

In certain non-limiting embodiments, the antibiotic/BPEI composition is formulated to contain a mass ratio in a range of 100:1 (e.g., 100 mg antibiotic per 1 mg of BPEI additive), to 1:1 (1 mg antibiotic per 1 mg BPEI), to 1:100 (1 mg antibiotic per 100 mg BPEI), or more particularly, a mass ratio in a range of 75:1 (e.g., 75 mg antibiotic per 1 mg of BPEI additive), to 1:1 (1 mg antibiotic per 1 mg BPEI), to 1:75 (1 mg antibiotic per 75 mg BPEI), or more particularly, a mass ratio in a range of 64:1 (e.g., 64 mg antibiotic per 1 mg of BPEI additive), to 1:1 (1 mg antibiotic per 1 mg BPEI), to 1:64 (1 mg antibiotic per 64 mg BPEI), or more particularly, a mass ratio in a range of 50:1 (e.g., 50 mg antibiotic per 1 mg of BPEI additive), to 1:1 (1 mg antibiotic per 1 mg BPEI), to 1:50 (1 mg antibiotic per 50 mg BPEI), or more particularly, a mass ratio in a range of 32:1 (e.g., 32 mg antibiotic per 1 mg of BPEI additive), to 1:1 (1 mg antibiotic per 1 mg BPEI), to 1:32 (1 mg antibiotic per 32 mg BPEI), or more particularly, a mass ratio in a range of 24:1 (e.g., 24 mg antibiotic per 1 mg of BPEI additive), to 1:1 (1 mg antibiotic per 1 mg BPEI), to 1:24 (1 mg antibiotic per 24 mg BPEI), or more particularly, a mass ratio in a range of 16:1 (e.g., 16 mg antibiotic per 1 mg of BPEI additive), to 1:1 (1 mg antibiotic per 1 mg BPEI), to 1:16 (1 mg antibiotic per 16 mg BPEI), or more particularly, a mass ratio in a range of 10:1 (e.g., 10 mg antibiotic per 1 mg of BPEI additive), to 1:1 (1 mg antibiotic per 1 mg BPEI), to 1:10 (1 mg antibiotic per 10 mg BPEI), or more particularly, a mass ratio in a range of 8:1 (e.g., 8 mg antibiotic per 1 mg of BPEI additive), to 1:1 (1 mg antibiotic per 1 mg BPEI), to 1:8 (1 mg antibiotic per 8 mg BPEI), or more particularly, a mass ratio in a range of 4:1 (e.g., 4 mg antibiotic per 1 mg of BPEI additive), to 1:1 (1 mg antibiotic per 1 mg BPEI), to 1:4 (1 mg antibiotic per 4 mg BPEI), or any range comprising a combination of said ratio endpoints, such as for example, a mass ratio in a range of 64:1 (e.g., 64 mg antibiotic per 1 mg of BPEI additive), to 1:4 (1 mg antibiotic per 4 mg BPEI), or a mass ratio in a range of 32:1 (e.g., 32 mg antibiotic per 1 mg of BPEI additive), to 1:16 (1 mg antibiotic per 16 mg BPEI).

In certain non-limiting embodiments, the dosage of the antibiotic/BPEI composition administered to a subject could be in a range of 1 µg per kg of subject body mass to 1000 mg/kg, or in a range of 5 µg per kg to 500 mg/kg, or in a range of 10 µg per kg to 300 mg/kg, or in a range of 25 µg per kg to 250 mg/kg, or in a range of 50 µg per kg to 250 mg/kg, or in a range of 75 µg per kg to 250 mg/kg, or in a range of 100 µg per kg to 250 mg/kg, or in a range of 200 µg per kg to 250 mg/kg, or in a range of 300 µg per kg to 250 mg/kg, or in a range of 400 µg per kg to 250 mg/kg, or in a range of 500 µg per kg to 250 mg/kg, or in a range of 600 µg per kg to 250 mg/kg, or in a range of 700 µg per kg to 250 mg/kg, or in a range of 800 µg per kg to 250 mg/kg, or in a range of 900 µg per kg to 250 mg/kg, or in a range of 1 mg per kg to 200 mg/kg, or in a range of 1 mg per kg to 150 mg/kg, or in a range of 2 mg per kg to 100 mg/kg, or in a range of 5 mg per kg to 100 mg/kg, or in a range of 10 mg compound per kg to 100 mg/kg, or in a range of 25 mg per kg to 75 mg/kg. For example, in certain non-limiting embodiments, the composition could contain antibiotic in a range of 0.1 mg/kg to 10 mg/kg, and BPEI in a range of 0.1 mg/kg to 10 mg/kg, or any range comprising a combination of said ratio endpoints, such as, for example, a range of 10 µg/kg to 10 mg/kg of the antibiotic/BPEI composition.

The BPEI used in the present formulations may have a molecular weight in a range of, for example, from 0.1 kDa (kilodaltons), to 0.25 kDa, to 0.50 kDa, to 0.75 kDa, to 1.0 kDa, to 2 kDa, to 3 kDa, to 4 kDa, to 5 kDa, to 6 kDa, to 7 kDa, to 8 kDa, to 9 kDa, to 10 kDa, to 12.5 kDa, to 15 kDa, to 17.5 kDa, to 20 kDa, to 22.5 kDa, to 25 kDa, including any fractional or integeric value within said range. Also, the percentage of primary amine-to-secondary amine-to-tertiary amine in the BPEI can be varied. For example, the BPEI may have a higher primary amine content as compared to the secondary amine and/or tertiary amine content.

The antibiotic and BPEI can be administered together in a single formulation (dose), or together (simultaneously) in separate formulations (doses), or sequentially, whereby administration of the antibiotic dosage is followed by the BPEI dosage, or administration of the BPEI dosage is followed by administration of the antibiotic dosage. The dosage(s) can be administered, for example but not by way of limitation, on a one-time basis, or administered at multiple times (for example but not by way of limitation, from one to five times per day, or once or twice per week), or continuously via a venous drip, depending on the desired therapeutic effect. In one non-limiting example of a therapeutic method of the presently disclosed inventive concepts, the composition is provided in an IV infusion. Administration of the compounds used in the pharmaceutical composition or to practice the method of the presently disclosed inventive concepts can be carried out in a variety of conventional ways, such as, but not limited to, orally, by inhalation, rectally, or by cutaneous, subcutaneous, intraperitoneal, vaginal, or intravenous injection. Oral formulations may be formulated such that the compounds pass through a portion of the digestive system before being released, for example it may not be released until reaching the small intestine, or the colon.

When a therapeutically effective amount of the composition(s) is administered orally, it may be in the form of a solid or liquid preparations such as capsules, pills, tablets, lozenges, melts, powders, suspensions, solutions, elixirs or emulsions. Solid unit dosage forms can be capsules of the ordinary gelatin type containing, for example, surfactants, lubricants, and inert fillers such as lactose, sucrose, and cornstarch, or the dosage forms can be sustained release preparations. The pharmaceutical composition(s) may contain a solid carrier, such as a gelatin or an adjuvant. The tablet, capsule, and powder may contain from about 0.05 to about 95% of the active substance compound by dry weight. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition(s) may further contain physiological saline solution, dextrose or other saccharide solution, or glycols such as ethylene glycol, propylene glycol, or polyethylene glycol. When administered in liquid form, the pharmaceutical composition(s) particularly contains from about 0.005 to about 95% by weight of the active substance. For example, a dose of about 10 mg to about 1000 mg once or twice a day could be administered orally.

In another embodiment, the composition(s) of the present disclosure can be tableted with conventional tablet bases such as lactose, sucrose, and cornstarch in combination with binders, such as acacia, cornstarch, or gelatin, disintegrating agents such as potato starch or alginic acid, and a lubricant such as stearic acid or magnesium stearate. Liquid preparations are prepared by dissolving the composition(s) in an aqueous or non-aqueous pharmaceutically acceptable solvent which may also contain suspending agents, sweetening agents, flavoring agents, and preservative agents as are known in the art.

For parenteral administration, for example, the composition(s) may be dissolved in a physiologically acceptable pharmaceutical carrier and administered as either a solution or a suspension. Illustrative of suitable pharmaceutical carriers are water, saline, dextrose solutions, fructose solutions, ethanol, or oils of animal, vegetative, or synthetic origin. The pharmaceutical carrier may also contain preservatives and buffers as are known in the art.

When a therapeutically effective amount of the composition(s) is administered by intravenous, cutaneous, or subcutaneous injection, the compound is particularly in the form of a pyrogen-free, parenterally acceptable aqueous solution or suspension. The preparation of such parenterally acceptable solutions, having due regard to pH, isotonicity, stability, and the like, is well within the skill in the art. A particular pharmaceutical composition for intravenous, cutaneous, or subcutaneous injection may contain, in addition to the active agent(s), an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition(s) of the present disclosure may also contain stabilizers, preservatives, buffers, antioxidants, or other additives known to those of skill in the art.

As noted, particular amounts and modes of administration can be determined by one skilled in the art. One skilled in the art of preparing formulations can readily select the proper form and mode of administration, depending upon the particular characteristics of the composition(s) selected, the infection to be treated, the stage of the infection, and other relevant circumstances using formulation technology known in the art, described, for example, in *Remington: The Science and Practice of Pharmacy*, 21$^{st}$ ed.

Additional pharmaceutical methods may be employed to control the duration of action of the composition(s). Increased half-life and/or controlled release preparations may be achieved through the use of polymers to conjugate, complex with, and/or absorb the active substances described herein. The controlled delivery and/or increased half-life may be achieved by selecting appropriate macromolecules (for example but not by way of limitation, polysaccharides, polyesters, polyamino acids, homopolymers polyvinyl pyrrolidone, ethylenevinylacetate, methylcellulose, or carboxymethylcellulose, and acrylamides such as N-(2-hydroxypropyl) methacrylamide), and the appropriate concentration of macromolecules as well as the methods of incorporation, in order to control release. The compound(s) may also be ionically or covalently conjugated to the macromolecules described above.

Another possible method useful in controlling the duration of action of the composition(s) by controlled release preparations and half-life is incorporation of the composition(s) or functional derivatives thereof into particles of a polymeric material such as polyesters, polyamides, polyamino acids, hydrogels, poly(lactic acid), ethylene vinylacetate copolymers, copolymer micelles of, for example, polyethylene glycol (PEG) and poly(l-aspartamide).

Examples of bacterial families which contain bacterial species against which the presently disclosed compositions and treatment protocols are effective include, but are not limited to:

Alicyclobacillaceae, Bacillaceae, Listeriaceae, Paenibacillaceae, Pasteuriaceae, Planococcaceae, Sporolactobacillaceae, Staphylococcaceae, Thermoactinomycetaceae, Aerococcaceae, Carnobacteriaceae, Enterococcaceae, Lactobacillaceae, Leuconostocaceae, Streptococcaceae, Caldicoprobacteraceae, Christensenellaceae, Clostridiaceae, Defluviitaleaceae, Eubacteriaceae, Graciibacteraceae, Heliobacteriaceae, Lachnospiraceae, Oscillospiraceae, Peptococcaceae, Peptostreptococcaceae, Ruminococcaceae, Syntrophomonadaceae, Veillonellaceae, Halanaerobiaceae, Halobacteroidaceae, Natranaerobiaceae, Thermoanaerobacteraceae, Thermodesulfobiaceae.

Specific bacteria that can be treated with the compositions and methods of the present disclosure include, but are not limited to:

*Enterococcus faecalis*, *Enterococcus faecium*, *Staphylococcus aureus*, Methicillin-resistant *Staphylococcus aureus* (MRSA), oxacillin-resistant *Staphylococcus aureus* (ORSA), vancomycin-resistant *Staphylococcus aureus* (VRSA), *Streptococcus pneumonia*, e.g., penicillin-resistant *Streptococcus pneumonia*, *Streptococcus mutans*, *Streptococcus sanguinis*, *Staphylococcus epidermidis*, *Bacillus anthracis*, *Bacillus cereus*, *Clostridium botulinum*, *Clostridium botulinum*, and *Listeria monocytogenes*.

EXAMPLES

The inventive concepts of the present disclosure will now be discussed in terms of several specific, non-limiting, examples. The examples described below, which include particular embodiments, will serve to illustrate the practice of the present disclosure, it being understood that the particulars shown are by way of example and for purposes of illustrative discussion of particular embodiments of the present disclosure only and are presented in the cause of providing what is believed to be a useful and readily understood description of procedures as well as of the principles and conceptual aspects of the inventive concepts.

In certain embodiments of the present disclosure, BPEI with an average molecular weight of 0.5 kDa was investigated for in vitro antimicrobial activity, and in certain embodiments synergy, with various antibiotics, including β-lactams, against MRSA. The results demonstrated that MRSA was re-sensitized to β-lactams at previously ineffective levels by the addition of BPEI. Likewise, a dramatic synergistic effect was seen with chloramphenicol, a drug that is used rarely in humans due to harmful side effects. However, BPEI did not show synergy with vancomycin or novobiocin antibiotics. Additionally, it was demonstrated that BPEI interacts with the cell wall of MRSA using laser scanning confocal microscopy (LSCM) images taken with BPEI conjugated to AlexaFluor 488, a fluorescent molecule. Without wishing to be bound by theory, these studies, using whole cells of MRSA, indicate a possible mode of action for BPEI's antimicrobial and synergistic properties that involves binding to the cell wall. PBP2a, located in the cell wall, is inactivated by antibiotics that prevent the synthesis of anionic teichoic acid polymers required for proper localization of the PBP2a enzyme. This function is in contrast to the common paradigm of directly targeting the enzyme. If BPEI binds to the cell wall, it may interrupt the function of teichoic acids, inactivate PBP2a and restore β-lactam activity. The cytotoxicity of BPEI was investigated using in vitro assays with murine fibroblast cells, revealing a low toxicity towards mammalian cells at concentrations resulting in antibiotic synergy. Lastly, the effectiveness of ampicillin towards non-resistant *S. aureus* was not affected by BPEI. These results indicate a dramatic benefit to human health, for example by using an ampicillin-BPEI combination, as a routine antibiotic therapy, to eliminate *S. aureus* infections while simultaneously preventing the growth of ampicillin-resistant bacteria.

Materials and Methods

Materials

The bacteria used in this work were obtained from the American Type Culture Collection (methicillin-resistant *Staphylococcus aureus* (MRSA) strain ATCC 700787, *Staphylococcus aureus* ATCC 25923, *Escherichia coli* ATCC 11775, *Bacillus subtilis* (Ehrenberg) Cohn ATCC 23059). Chemicals from Sigma-Aldrich (e.g., DMSO, ampicillin, methicillin, vancomycin, chloramphenicol, and novobiocin) were used as purchased.

Preparation and Characterization of Cationic Polymers

Branched and linear polyethylenimine was obtained from Sigma-Aldrich, Inc. as high molecular weight (~25 kDa) or low molecular weight (~0.5 kDa) polymers. The molecule has polycationic character from the protonation of its amine functional groups based on its protonation constant ($pK_a$). Protonation constants for branched PEI molecules have been reported to be around 4.5 for primary amines, 6.7 for secondary amines, and 11.6 for tertiary amines.[20] Thus, at pH=7.2, the BPEI has many positively-charged primary amines to interact with teichoic acid.

Growth Inhibition Assays

Compounds were tested against methicillin-resistant *Staphylococcus aureus* (MRSA) strain ATCC 700787, which also exhibits reduced susceptibility to vancomycin. A stock culture was diluted in tryptic soy broth (TSB) and delivered into pre-sterilized 96-well plates. Stock solutions of BPEI and antibiotics, prepared in DMSO, were added to each well of a 96-well plate (final DMSO concentration was 1%), followed by inoculation with MRSA in TSB. Optical density measurements were performed with a Tecan Infinite M200 plate reader and an initial $OD_{600}$ value recorded. The plates were incubated for 20 h in a humidified incubator at 37° C. Plates were removed, orbitally shaken, and a final $OD_{600}$ value recorded. The final $OD_{600}$ reading was subtracted from the initial $OD_{600}$ reading to obtain the change in $OD_{600}$ (recorded in the figures as $\Delta OD_{600}$). Antimicrobial activity was determined by the change in optical density. Duplicate measurements were performed and the average reported.

Using the average $\Delta OD_{600}$ values, separate MIC values for BPEI and ampicillin were determined by the lowest concentration of each that inhibited growth. From this, fractional inhibitory concentration indices (FIC) were calculated for all wells that showed inhibition.[21, 22]

Cytotoxicity Assay

Mammalian cell cytotoxicity assays were performed on NIH/3T3 mouse fibroblast cells by adding 5,000 cells per well into 96-well plates. The cells were allowed to adhere overnight at 37° C. in a humidified incubator (5% $CO_2$ atmosphere). Test compounds were diluted in DMSO and added to the wells so that the final concentration of DMSO per well did not exceed 1% by volume. The plates containing treated and control cells were incubated for 48 hours and cell viability was determined by MTT assay.[23] Duplicate measurements were performed and the average reported.

Synthesis of the BPEI:Dye Conjugate

Low-molecular weight BPEI (Sigma-Aldrich) was added to Alexa Fluor 488 dye provided in the Alexa Fluor 488 Protein Labeling Kit (Life Technologies) at a ratio of 200 μL BPEI (3 mg/mL stock in Milli-Q $H_2O$) per tube of powdered dye. After allowing the dye and BPEI to form the conjugate over 1.5 h at 25° C., the product was stored at 4° C. and used without further purification.

Labeling MRSA Cells With the BPEI:Dye Conjugate

Cultures of *E. coli* ATCC 11775 and methicillin-resistant *S. aureus* ATCC 700787 at mid-log growth phase were pelleted by centrifugation at 2,000×g for 5 minutes at room temperature, and the growth media supernatant was removed. 6 μM DAPI in phosphate-buffered saline (1×PBS, pH 7.2) was added to resuspend the cell pellet, which was allowed to incubate for 5 minutes at room temperature. The BPEI-dye conjugate was then added to a final concentration of 100 μg/mL. Two control samples were prepared with either unconjugated BPEI or Alexa Fluor 488 alone and added to MRSA cells as described above. The stained bacterial cells were immediately fixed by resuspension with 4% paraformaldehyde (PFA) followed by a 10-fold dilution in 1×PBS. Cells were added to a microscope slide immediately prior to imaging.

Confocal Microscopy

PFA-fixed cells were mounted in 1×PBS and imaged using a Leica SP8 LSCM with a 63x/1.4NA oil objective. A 405 nm GaN diode laser line was used to image DAPI, and a 488 nm argon laser line was used to observe Alexa Fluor 488 fluorescence. Single optical sections were acquired of cells that had adhered to the coverslip, for highest axial resolution, with a pixel resolution of 80 nm×80 nm. Instrument settings were kept fixed for all imaging to allow for direct comparison of fluorescence intensity.

Image Processing

To visualize the relative localization of fluorescence, independent of intensity, images were processed (ImageJ v1.49m) such that the total fluorescence intensity within each image was visible (Figure S8, left column). To determine the relative fluorescence intensity between images, the fluorescence intensity of both the DAPI and the Alexa Fluor 488 were normalized to the respective intensities in the MRSA sample treated with BPEI conjugated with Alexa Fluor 488 (Figure S8, right column).

WTA Purification For NMR Studies

The NMR experiments require 1-5 mg WTA isolated from 1 L of bacterial cell culture. The poly(ribitol phosphate) WTA used in this work was isolated from *B. subtilis* W23[24, 25] (*Bacillus subtilis* (Ehrenberg) Cohn ATCC® 23059™) rather than from MRSA, allowing high volumes (500-2000 mL) of culture to be processed with minimal risk to personnel. This also allows us to take the sample into the NMR facility room which is not rated for BSL-2 work. In the rare instance of sample breakage, using WTA from *B. subtilis* W23 does not present a clean-up hazard nor require decontamination of the expensive NMR analysis probes, magnets, or spectrometers.

*B. subtilis* W23 cells were grown in LB broth to an $OD_{600}$ reading of approximately 0.8. After growth, the cells were harvested by centrifugation and physically disrupted using an Avestin® EmulsiFlex-C3 homogenizer. The insoluble cell wall was collected, placed in boiling 6% (w/v) SDS, washed with sterile water and EDTA then placed in a 10% trichloroacetic acid (TCA) treatment for 48 hours at 4° C. After allowing the TCA to remove the bound WTA from the cell wall, the WTA was collected in the supernatant and placed into a 500 Da molecular weight cutoff dialysis membrane. Membrane dialysis was performed at 4° C. in 1.5 L of sterile water with continual water changes over a 24-hour period. The final 4 h of dialysis took place in a 1 kDa molecular weight cutoff membrane to assure sample purity. The sample was lyophilized and kept at −20° C. until use.

NMR Spectroscopy

NMR samples were prepared in Eppendorf tubes by mixing teichoic acid with low-$M_w$ BPEI in water. The pH was measured with a microscopic pH probe and adjusted to 7.2 if necessary. A 3-mm NMR tube was filled with 160 μL of a 2 mM sample of WTA/$D_2O$ or a combination of 2 mM BPEI with 2 mM WTA in $D_2O$. NMR data collection use Agilent VNMRS-500 MHz equipped with a PFG probe tuned to the $^{31}P$ resonance frequency. Data acquisition and processing were performed using VNMRJ 2.2C software on a system running Red Hat Enterprise Linux.

Results and Discussion

Figure 2:
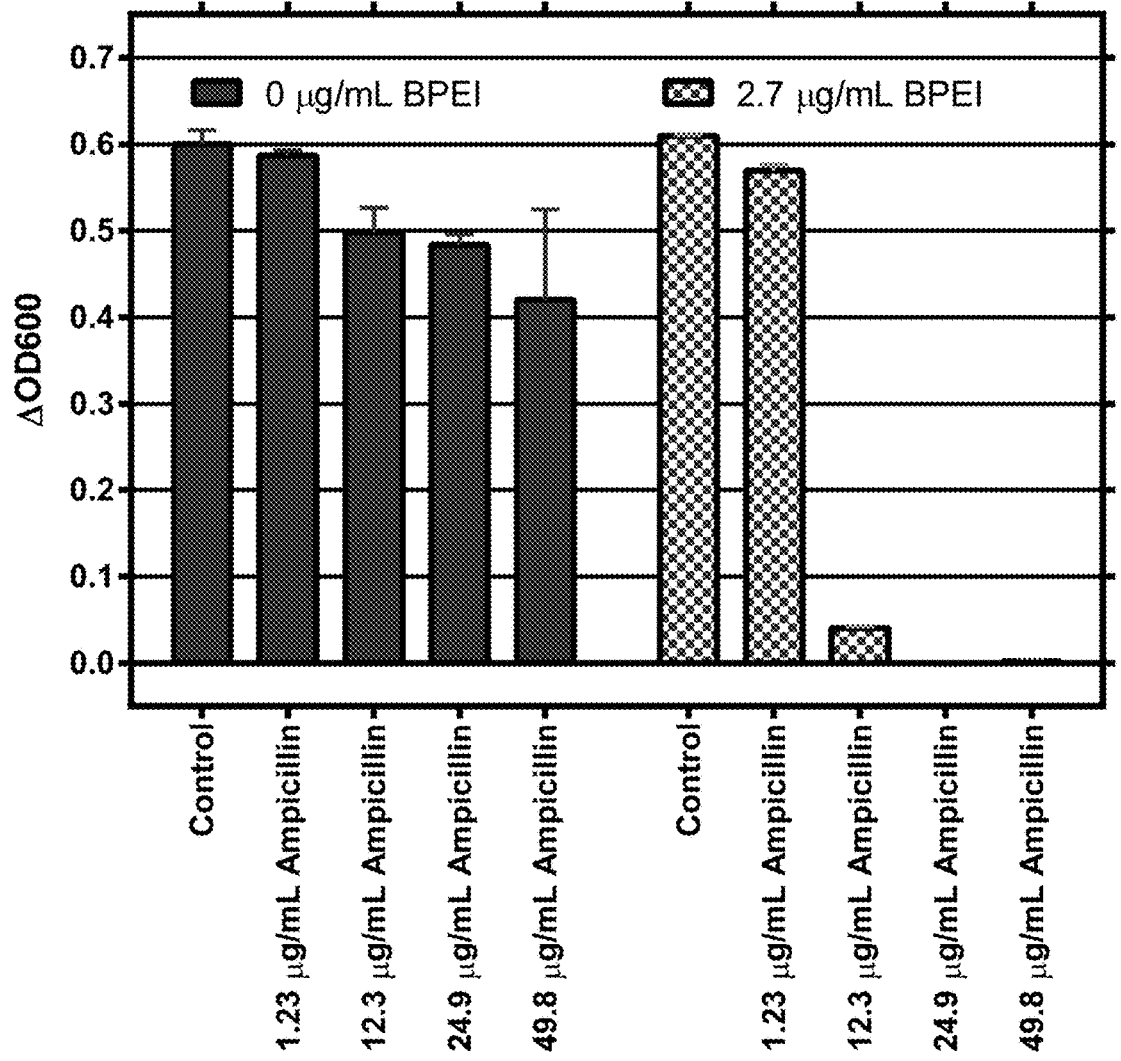
FIG. 2 shows results of an in vitro assay of ampicillin against MRSA. When BPEI (2.7 µg/mL) is added, the MIC for ampicillin is between 12 and 25 µg/mL (checkered columns) while ampicillin without BPEI does not inhibit MRSA below 50 µg/mL concentration (solid columns). The growth of MRSA was evaluated by measuring the change in $OD_{600}$ after 20 hours. Cell growth in TSB without additives is denoted as Control.
Figure 3:
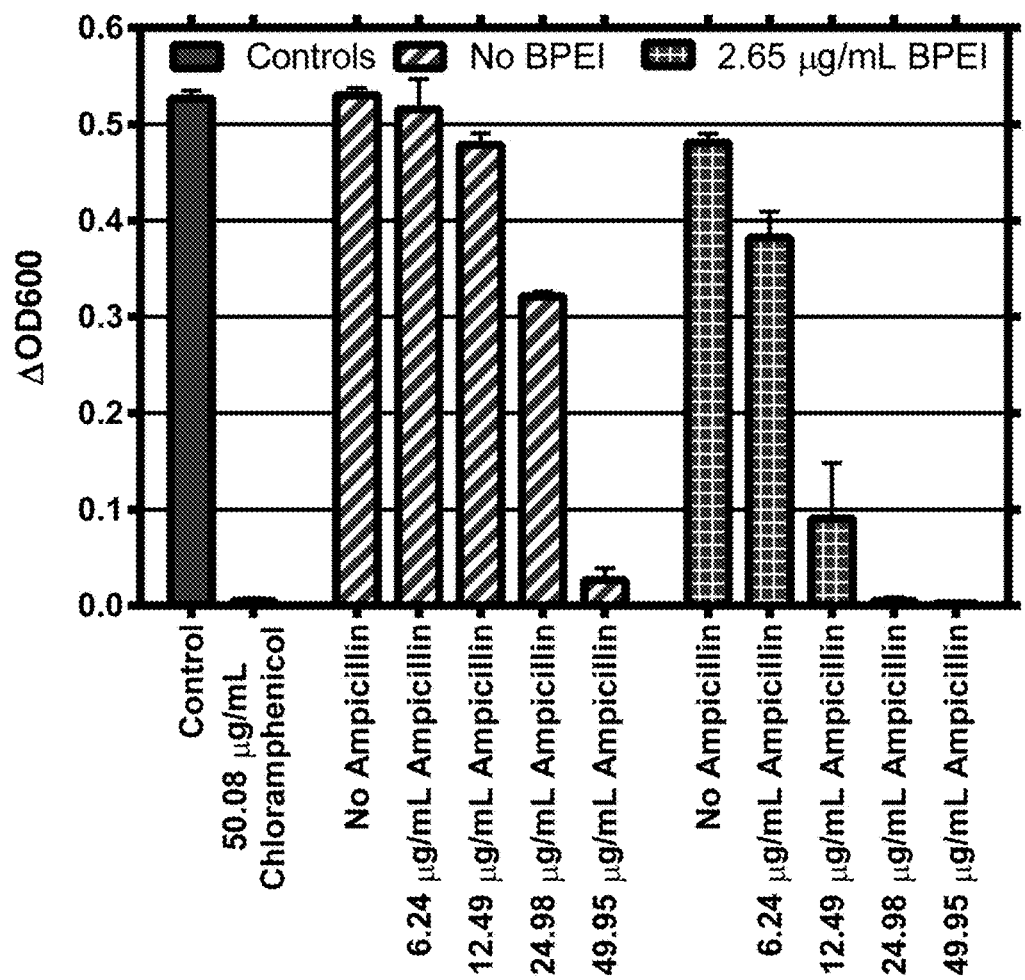
FIG. 3 shows results of an in vitro assay of ampicillin against MRSA. When BPEI (2.7 µg/mL) is added, the MIC for ampicillin is approximately 25 µg/mL (checkered columns); without BPEI, the MIC is approximately 50 µg/mL (solid columns). The growth of MRSA was evaluated by measuring the change in $OD_{600}$ after 20 hours. Cell growth in TSB without additives is denoted as Control; addition of 50 µg/mL chloramphenicol provided a negative control.

While there are numerous MRSA strains, *Staphylococcus aureus* subsp. *aureus* ATCC® 700787™ was isolated in Port Chester, N.Y. from blood culture, exhibits vancomycin intermediate resistant (VISA) and also expresses mecA to produce PBP2a. The effect of BPEI concentration on ampicillin effectiveness is shown in FIGS. 1-3, 5 and Table 1. The growth of MRSA in vitro after 20 hours of incubation was inhibited by ampicillin when the antibiotic was co-administered with low molecular-weight branched poly(ethylenimine), low-$M_w$ BPEI. At a fixed ampicillin concentration of 9.3 µg/mL, BPEI shows synergy by inhibiting MRSA at a concentration of 5.3 µg/mL (FIG. 1). In the absence of ampicillin, BPEI itself can inhibit bacterial growth only at a concentration of 53 µg/mL, a tenfold increase (FIG. 1). As BPEI concentration is reduced, 9.3 µg/mL ampicillin becomes less able to inhibit the growth of MRSA. The ampicillin concentration was varied while the amount of BPEI was fixed at 2.7 µg/mL. This BPEI concentration, as observed in FIG. 1, produced attenuated but measurable growth in conjunction with 9.3 µg/mL ampicillin. As shown in FIG. 2, the minimum inhibitory concentration (MIC) is between 12-25 µg/mL ampicillin using 2.7 µg/mL of BPEI, and that ampicillin without added BPEI is ineffective against MRSA at or below 50 µg/mL. A second set of data confirmed that MRSA growth is slowed with 12-25 µg/mL ampicillin combined with 2.7 µg/mL BPEI yet shows that ampicillin alone does not inhibit MRSA growth at 25 µg/mL but does substantially at a higher concentration of 50 µg/mL (FIG. 3). Thus, in one embodiment the combination of ampicillin and The ability of BPEI to restore ampicillin effectiveness against MRSA is shown in Table 1. MRSA shows resistance towards ampicillin, with a minimum inhibitory concentration (MIC) of 32 µg/mL, but the presence of low-$M_w$ BPEI (16 µg/mL) rendered MRSA susceptible to ampicillin at a 32× lower dose (MIC=1 µg/mL). At a reduced BPEI concentration of 8 µg/mL, the ampicillin MIC was still decreased, but only to 8 µg/mL. In the absence of ampicillin, BPEI itself inhibited growth of MRSA at a concentration of 64 µg/mL. With these values, it is possible to calculate the fractional inhibitory concentration (FIC) index for each combination. When the FIC is equal to or below 0.5, ampicillin and low-$M_w$ BPEI stop MRSA growth through synergistic effects. Synergy occurred between 8 µg/mL ampicillin and 8 µg/mL low-$M_w$ BPEI (FIC=0.375), as well as with combinations of 16 µg/mL low-$M_w$ BPEI with 1, 2, 4, and 8 µg/mL ampicillin (FIC=0.281, 0.313, 0.275, 0.500 respectively). Although MRSA does not grow in the presence of 0.5 µg/mL ampicillin and 32 µg/mL low-$M_w$ BPEI, the FIC index is 0.516. Thus, in other embodiments, a combination which is slightly above 0.5 also inhibits the bacteria such as 0.52, 0.53, 0.54, or 0.55.

TABLE 1

MRSA Growth Inhibition Assay in the Presence of Ampicillin and low-Mw BPEI

| BPEI Conc. (µg/mL) | Ampicillin Concentration (µg/mL) | | | | | | | | | | |
|---|---|---|---|---|---|---|---|---|---|---|---|
| | 0 | 0.125 | 0.250 | 0.500 | 1 | 2 | 4 | 8 | 16 | 32 | 64 |
| 0 | 0.4887 | 0.4361 | 0.4282 | 0.4342 | 0.4289 | 0.4294 | 0.4375 | 0.4344 | 0.3287 | 0.0003 | 0.0014 |
| 1 | 0.5088 | 0.4124 | 0.4289 | 0.4310 | 0.4324 | 0.4283 | 0.4097 | 0.3943 | 0.0661 | 0.0024 | 0.0037 |
| 2 | 0.4937 | 0.4388 | 0.4374 | 0.4510 | 0.4372 | 0.4540 | 0.3814 | 0.2333 | 0.0062 | 0.0020 | 0.0021 |
| 4 | 0.5054 | 0.4217 | 0.4693 | 0.4289 | 0.4373 | 0.4115 | 0.2587 | 0.1954 | 0.0006 | 0.0033 | 0.0018 |
| 8 | 0.4835 | 0.4423 | 0.4449 | 0.4610 | 0.2826 | 0.2411 | 0.1070 | 0.0018 | 0.0011 | 0.0025 | 0.0002 |
| 16 | 0.4066 | 0.3178 | 0.2238 | 0.2931 | 0.0416 | 0.0053 | 0.0017 | 0.0012 | 0.0003 | 0.0006 | 0.0007 |
| 32 | 0.1860 | 0.0997 | 0.1531 | 0.0007 | 0.0798 | 0.0006 | 0.0022 | 0.0023 | 0.0009 | 0.0001 | 0.0002 |
| 64 | 0.0001 | 0.0012 | 0.0005 | 0.0003 | 0.0001 | 0.0003 | 0.0006 | 0.0018 | 0.0175 | 0.0003 | 0.0011 |

MRSA cells (ATCC 700787) were used to inoculate growth media containing ampicillin and low-Mw BPEI at 37° C. for 20 hours. Entries in Table 1 are optical density (OD) of the growth media measured at a wavelength of 600 nm. Each entry is the average of duplicate measurement. The bold line separates combinations that allowed MRSA growth ($OD_{600}$ values above 0.05) from those combinations that prevented MRSA growth. The ampicillin MIC is 32 µg/mL demonstrating antibiotic resistance without the presence of BPEI. Values highlighted in bold text were determined to arise from synergy between ampicillin and BPEI.

BPEI can inhibit the growth of MRSA in combinations of either 12 µg/mL ampicillin+2.7 µg/mL BPEI or 9.3 µg/mL ampicillin+5.3 µg/mL BPEI. A further increase in BPEI (26 µg/mL) causes a substantial reduction in the MIC of ampicillin (to approximately 1.2 µg/mL, FIG. 5).

Figure 6:
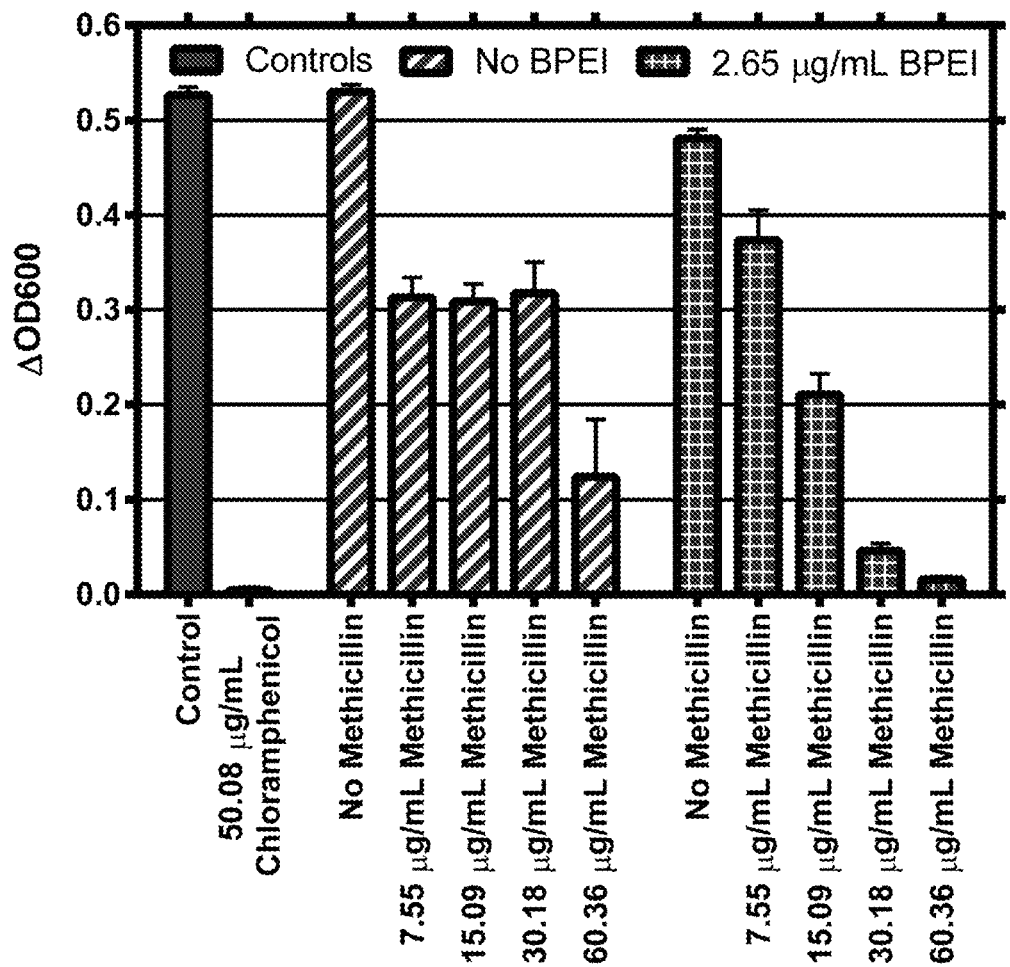
FIG. 6 shows results of an in vitro methicillin assay against MRSA. Addition of 2.65 µg/mL BPEI gives a methicillin MIC of ~30 µg/mL (thatched columns), while methicillin by itself does not completely inhibit MRSA growth at 60 µg/mL (striped columns). The growth of MRSA was evaluated by measuring the change in $OD_{600}$ after 20 hours. Cell growth in media without additives is denoted as Control, while addition of 50 µg/mL chloramphenicol serves as a negative control (solid columns).
Figure 7:
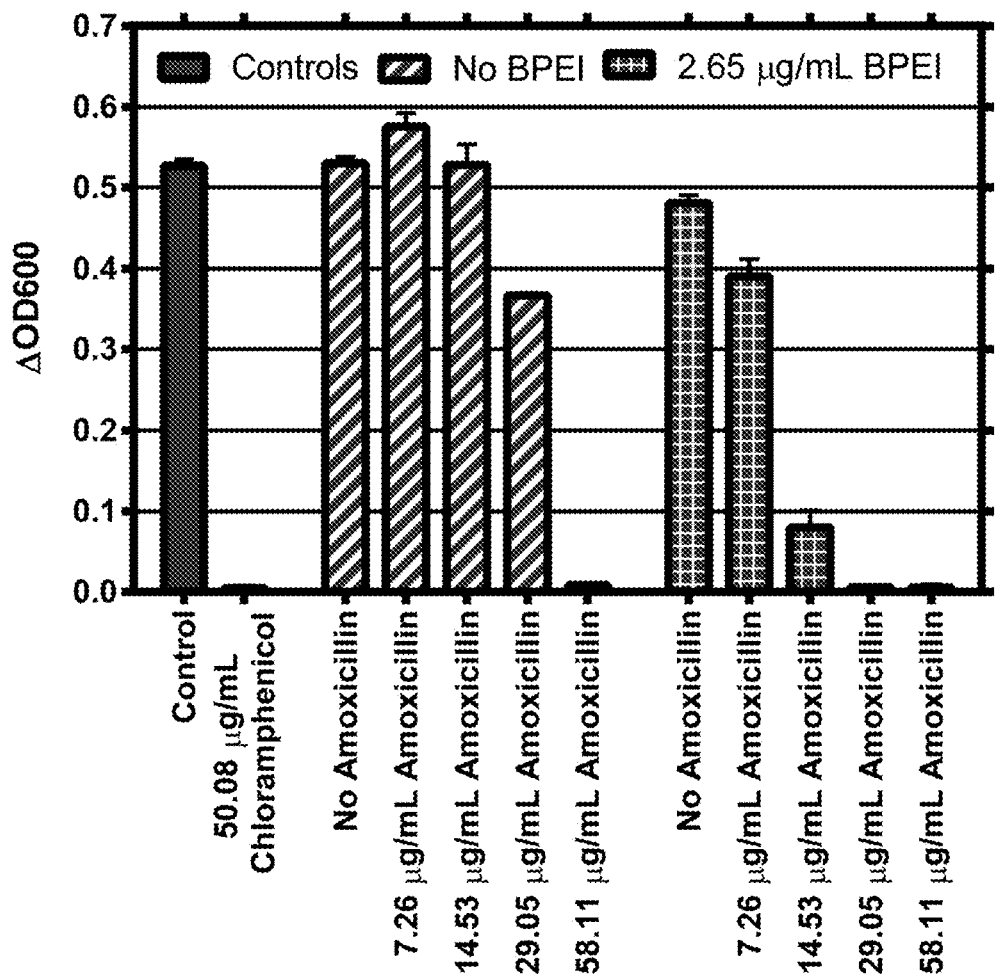
FIG. 7 shows results of an in vitro amoxicillin assay against MRSA. Addition of 2.65 µg/mL BPEI allows amoxicillin to inhibit MRSA growth at 29 µg/mL (thatched columns); the same level of inhibition requires 58 µg/mL amoxicillin without BPEI (striped columns). MRSA growth was evaluated by measuring the change in $OD_{600}$ after 20 hours. Cell growth in media without additives is denoted as Control; chloramphenicol addition (50 µg/mL) provides a negative control (solid columns).
Figure 8:
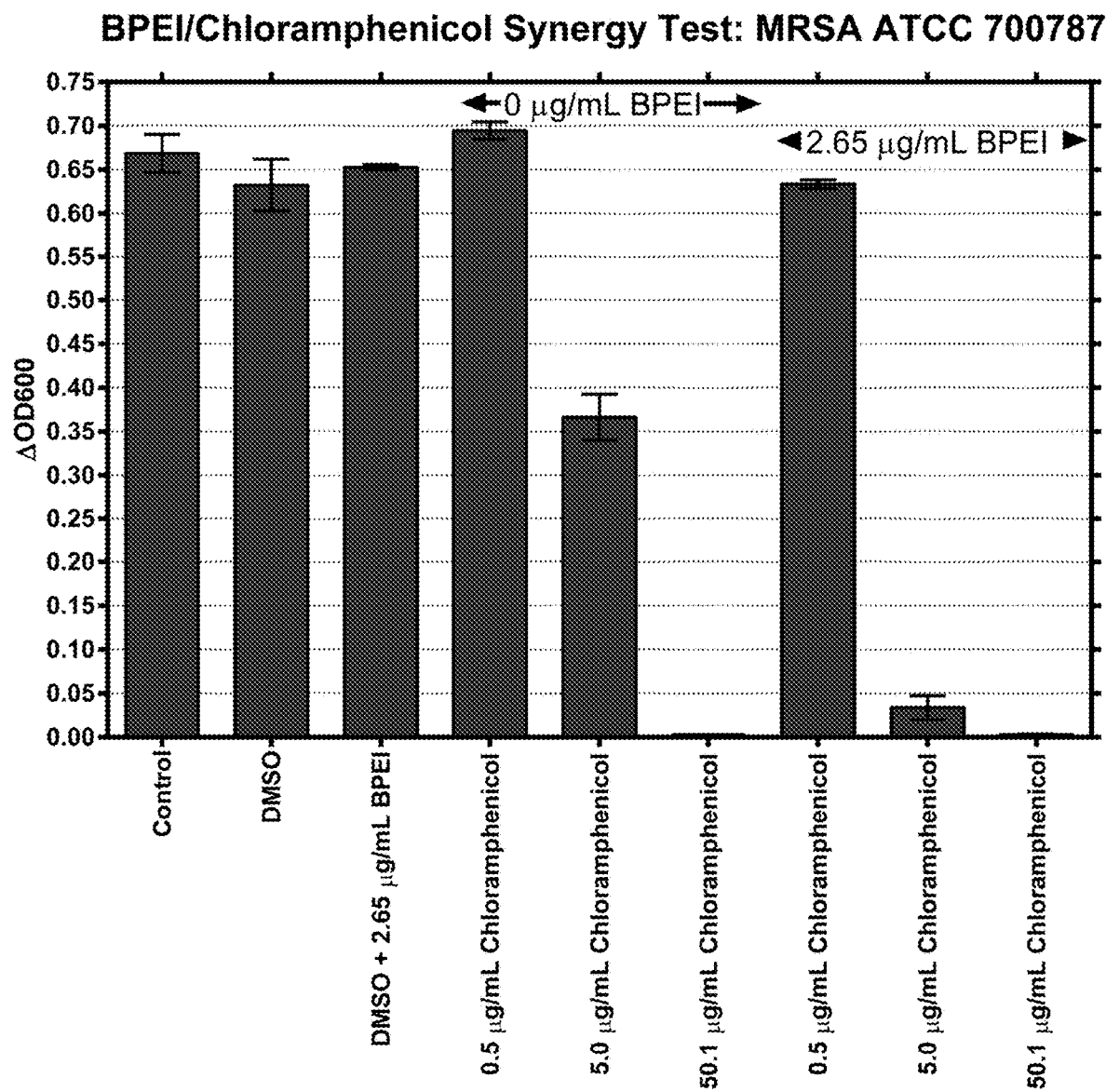
FIG. 8 shows results of an in vitro chloramphenicol assay against MRSA. MRSA is inhibited with the addition of 5 µg/mL chloramphenicol in conjunction with 2.65 µg/mL BPEI; without BPEI the chloramphenicol MIC is raised to 50 µg/mL. MRSA growth did not differ substantially between normal media (Control), media with 1% DMSO, and media with both DMSO and BPEI.
Figure 9:
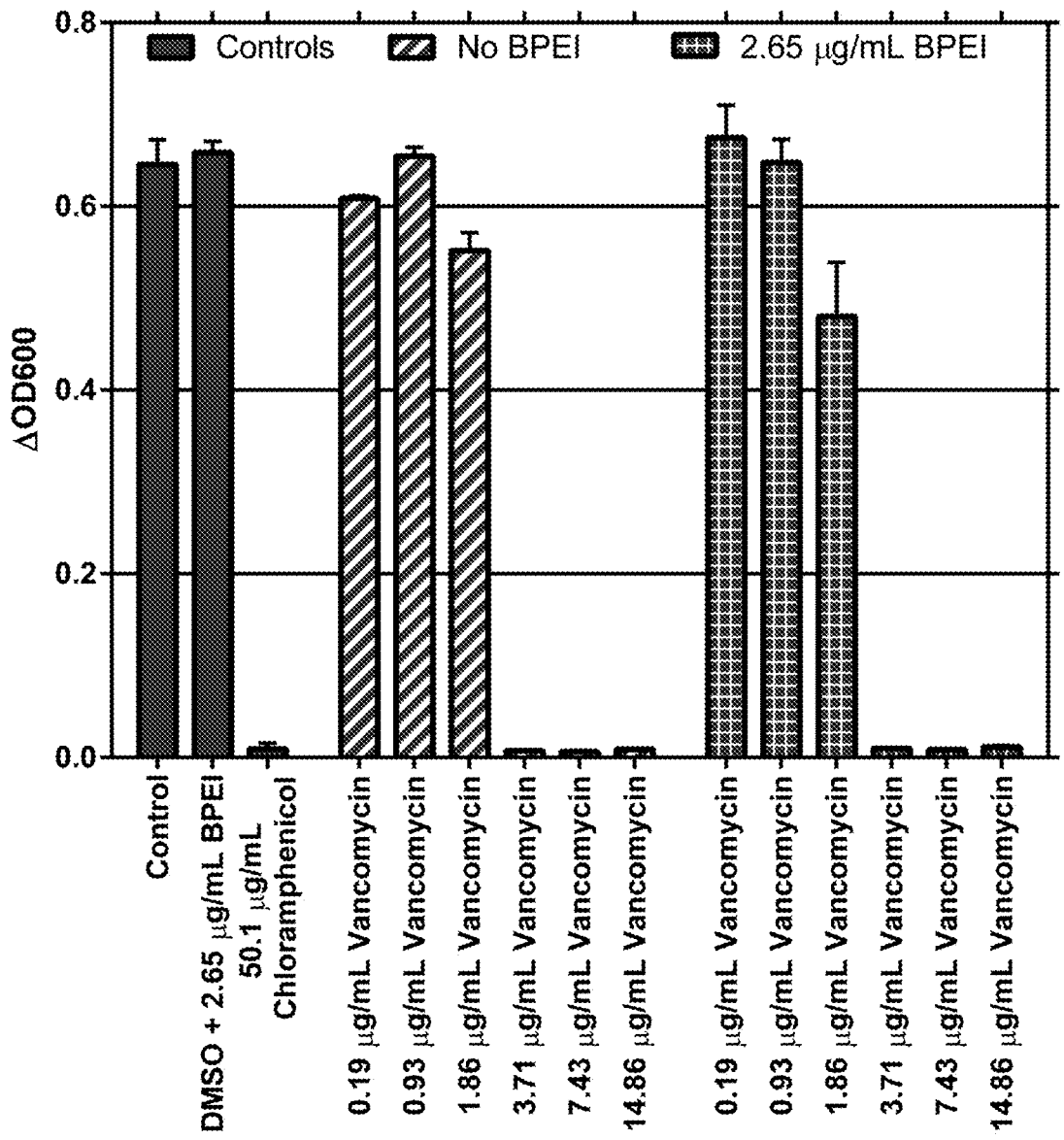
FIG. 9 shows results of an in vitro vancomycin assay against MRSA. The vancomycin MIC against MRSA does not change between antibiotic alone (striped columns) and addition of 2.65 µg/mL BPEI (thatched columns). The growth of MRSA was evaluated by measuring the change in $OD_{600}$ after 20 hours. Cell growth in media without additives is denoted as Control. Addition of BPEI and DMSO to the media does not hinder MRSA growth, while addition of 50 µg/mL chloramphenicol serves as a negative-growth control (solid columns).
Figure 10:
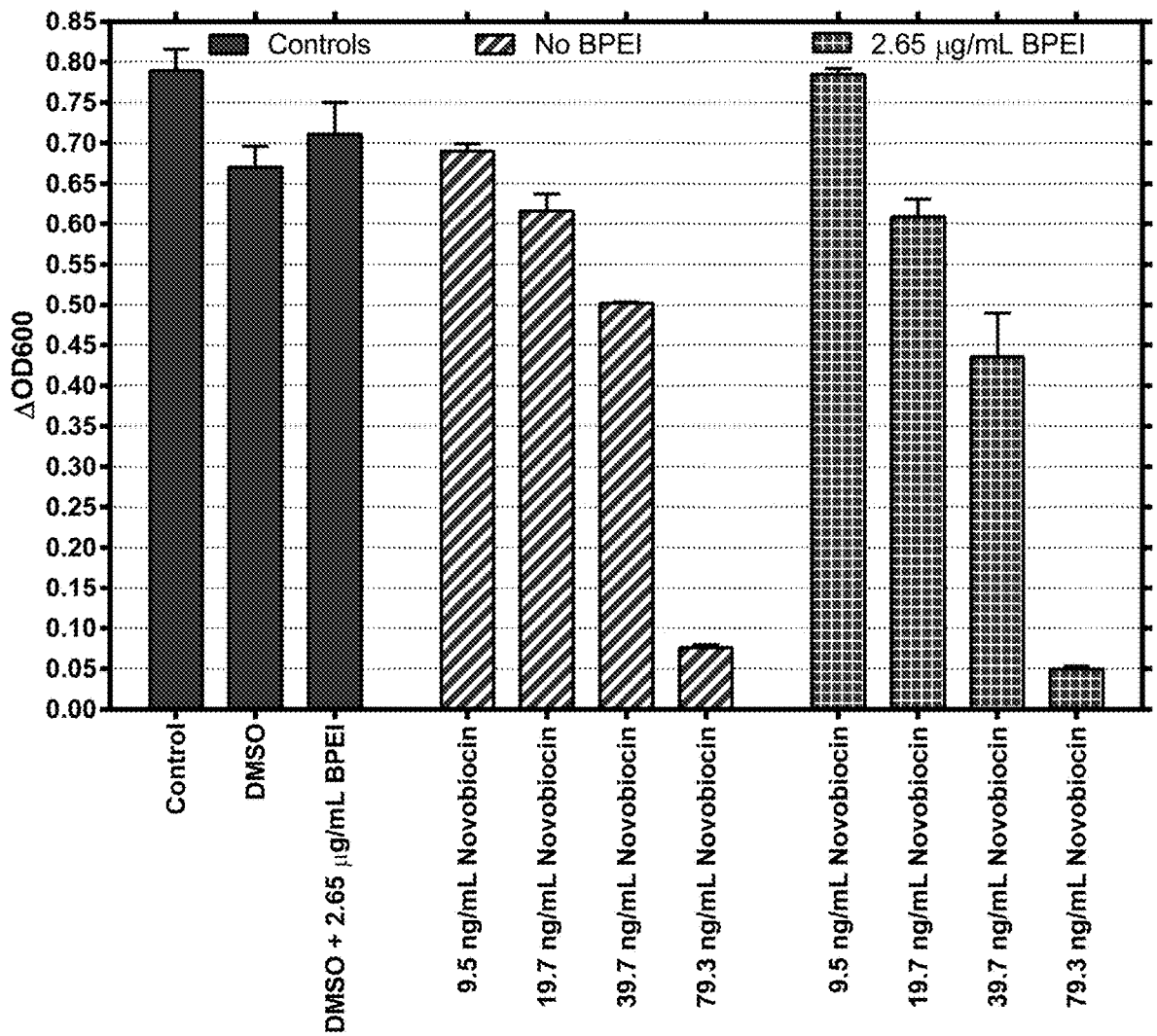
FIG. 10 shows results of an in vitro novobiocin assay against MRSA. Growth of MRSA is not substantially altered from novobiocin alone (striped columns) upon addition of 2.65 µg/mL BPEI (thatched columns). The growth of MRSA was evaluated by measuring the change in $OD_{600}$ after 20 hours. Positive growth controls (in media, media+DMSO, and media+DMSO+BPEI) are shown (solid columns).

The demonstrated synergistic effect between BPEI and ampicillin indicates that similar effects can be obtained with other may be seen with other β-lactam antibiotics. For the β-lactams methicillin and amoxicillin, 30 µg/mL was able to inhibit MRSA in the presence of 2.7 µg/mL BPEI (FIG. 6 and FIG. 7, respectively). Likewise, addition of 2.7 µg/mL BPEI induced a 10-fold decrease in the MIC for chloramphenicol (FIG. 8). BPEI did not show any synergy with vancomycin or novobiocin against MRSA (FIG. 9 and FIG. 10). The three β-lactam antibiotics showed increased efficacy, as did chloramphenicol, a member of the amphenicol class. However, novobiocin, an aminocoumarin, and vancomycin, a glycopeptide, showed no increased efficacy in combination with BPEI. Aminocoumarins work by inhibiting DNA gyrase. This differs from the mechanism of action of amphenicols, which work in the bacterial ribosome to inhibit protein synthesis. Glycopeptides inhibit peptidoglycan crosslinking by binding to the peptidoglycan stems, and β-lactams occupy active sites of transpeptidase proteins that create the crosslinks between two peptide stems.

Figure 11:
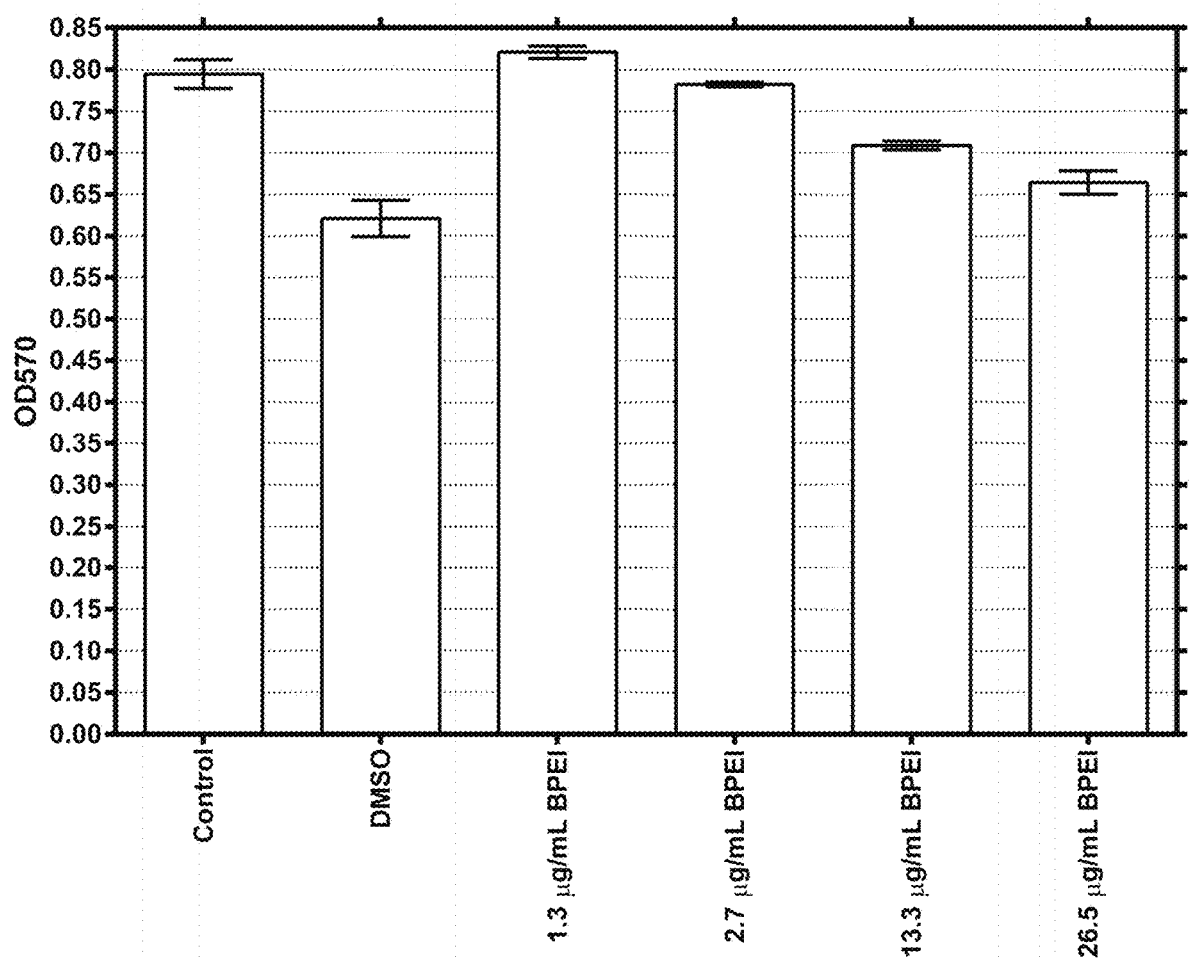
FIG. 11 shows results of an in vitro assay of BPEI toxicity against murine cells. Viability of NIH/3T3 mouse fibroblasts over three days was examined through $OD_{570}$ measurements. BPEI has little effect on proliferation or viability of 3T3 murine cells at up to the highest concentration tested, 26.5 µg/mL. Untreated cells are listed as the control; DMSO toxicity is shown for comparison.

The trend of lower ampicillin MIC with higher BPEI concentration suggests that superior therapeutic treatment of MRSA may occur as BPEI levels increase. However, BPEI must demonstrate low mammalian cytotoxicity to be clinically viable. It is known that most branched PEIs are nontoxic below 25 kDa MW. To test the cytotoxicity of BPEI used in these experiments (MW ~0.5 kDa), mouse fibroblasts (NIH/3T3 cells) were incubated over three days in the presence of varying concentrations of BPEI (FIG. 11). Viability was determined using the MTT assay, following the protocol of Hansen et al. At 2.65 µg/mL, only 1.5% of the fibroblasts became nonviable over the three-day incubation period compared against the control sample. This indicates negligible cytotoxicity from low-$M_w$ BPEI. From the checkerboard assay (Table 1), synergy occurs with 16 µg/mL low-$M_w$ BPEI which causes ~10% reduction in fibroblast viability (FIG. 11). At 26.5 µg/mL low-$M_w$ BPEI, only a 16.3% reduction in viability compared to the control sample was observed. Thus, BPEI concentrations that induce synergy are also associated with low cytotoxicity. Low-$M_w$ BPEI is non-toxic whereas high-$M_w$ BPEI penetrates mammalian cells leading to cytotoxicity and renal failure. Low-$M_w$ BPEI, up to 1000 µg/mL, does not affect the membrane of human cells as judged by the lack of hemolysis in red blood cells and the lack of lactate hydrogenase leakage from HEp-2 cells.[30] The BPEI concentration for this toxicity testing is ~25 times larger than the highest amount, 64 µg/mL, used for antibiotic potentiation.

Figure 12:
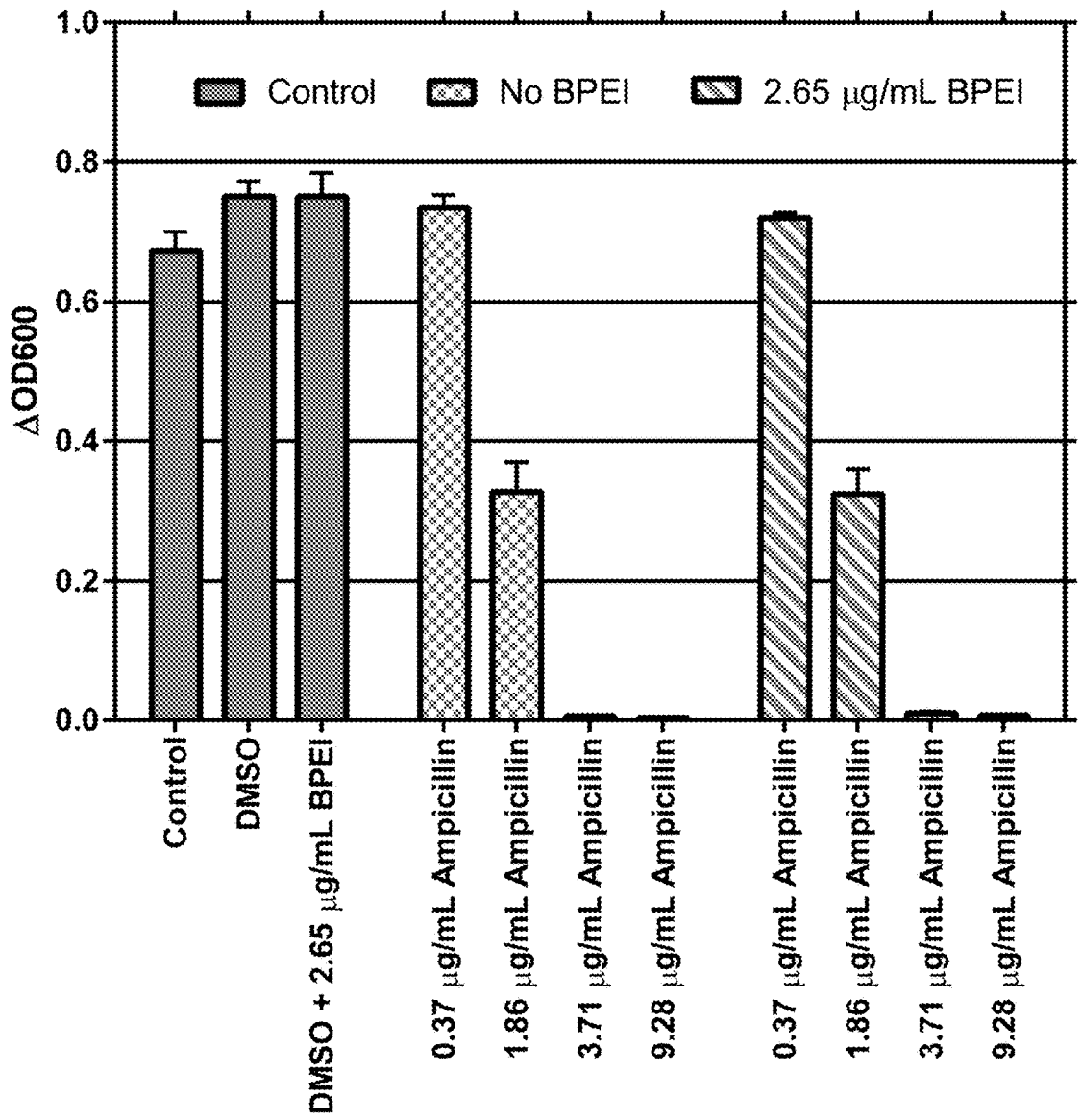
FIG. 12 shows results of an in vitro ampicillin assay against Gram-negative *E. coli*. When BPEI (2.65 µg/mL) is added, the MIC for ampicillin is approximately 3.7 µg/mL (striped columns), identical to that observed with ampicillin alone (checkered columns). The growth was evaluated by measuring the change in $OD_{600}$ after 20 hours. Cell growth in media without additives is denoted as Control, along with growth in media with 1% DMSO and DMSO+BPEI (solid columns).
Figure 13:
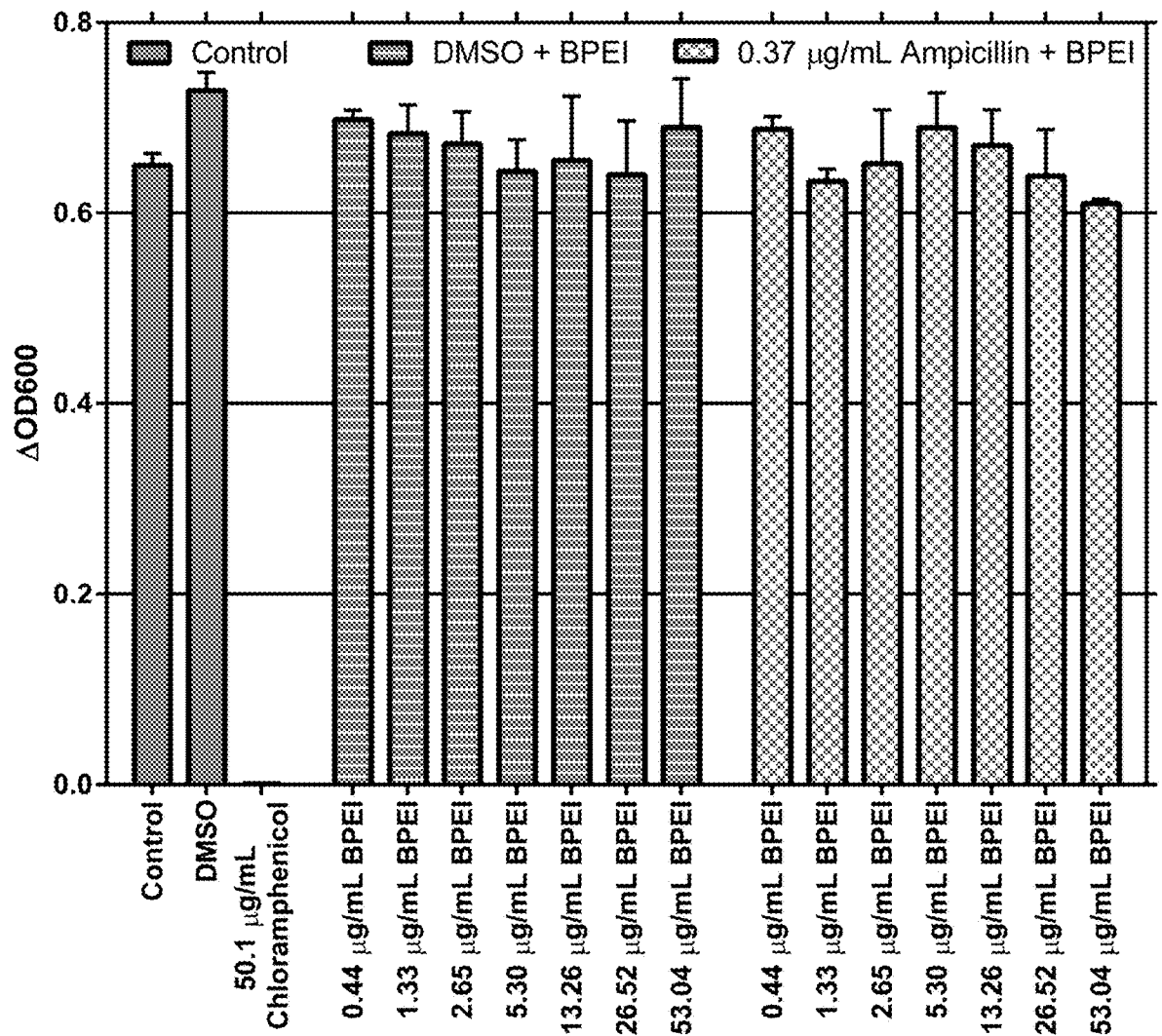
FIG. 13 shows results of an in vitro BPEI assay against Gram-negative *E. coli* bacteria. Addition of BPEI does not affect the growth of *E. coli*, either by itself (striped columns) or in conjunction with 3.7 µg/mL ampicillin (checkered columns). Growth of *E. coli* was evaluated by measuring the change in $OD_{600}$ after 20 hours. Cell growth in media without additives is denoted as Control and in media with 1% DMSO as DMSO; addition of 50 µg/mL chloramphenicol serves as a negative control (solid columns).

Antibiotic potentiation by BPEI does not extend to Gram-negative *Escherichia coli* (ATCC 11775). Results of growing *E. coli* in the presence of ampicillin alone and with a fixed BPEI concentration (2.65 µg/mL) are shown in FIG. 12. FIG. 13 shows the result of testing BPEI with a fixed ampicillin concentration (3.7 µg/mL). In the first data set (FIG. 12), the observed ampicillin MIC was identical at 3.7 µg/mL with or without BPEI addition. In the second data set (FIG. 13), BPEI did not show inhibitory effects on growth of *E. coli* up to 53 µg/mL, either by itself or with 3.7 µg/mL ampicillin. This is in contrast to the MRSA data in which the ampicillin MIC decreased by a factor of 32 when the BPEI concentration was 16 µg/mL. Additionally, our data differs from previously reported results showing PEI-induced antibiotic synergy against Gram-negative bacteria, including *E. coli* and *P. aeruginosa* when using a high-$M_w$ LPEI (instead of the low-$M_w$ BPEI used herein.

Figure 18:
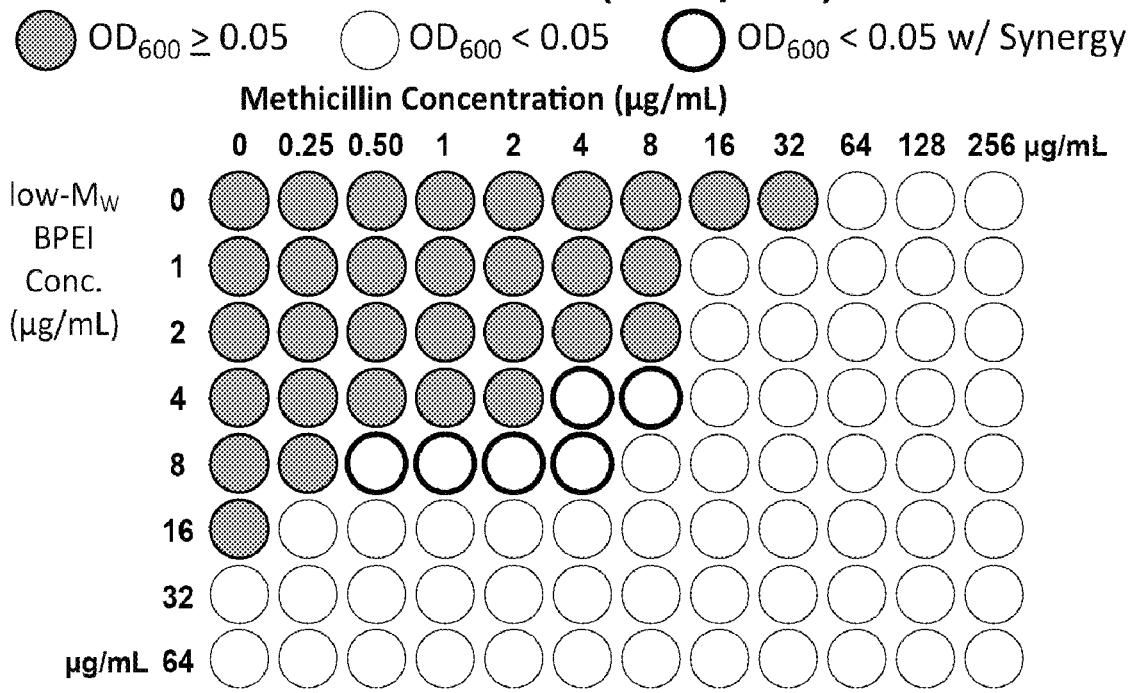
FIG. 18 shows an in vitro checkerboard assay of the effectiveness of BPEI in restoring methicillin efficacy against MRSA. An optical density ($OD_{600}$)<0.05 was used as an indicator of growth inhibition. Synergy was confirmed using FIC values.
Figure 19:
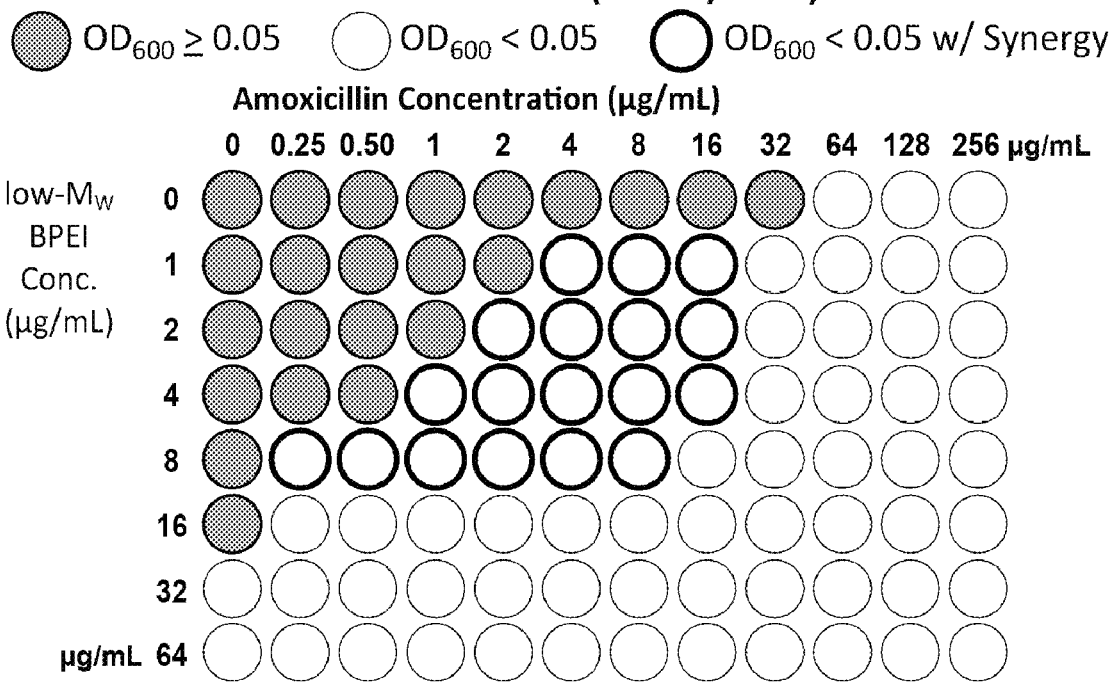
FIG. 19 shows an in vitro checkerboard assay of the effectiveness of BPEI in restoring ampicillin efficacy against MRSA. An optical density ($OD_{600}$)<0.05 was used as an indicator of growth inhibition. Synergy was confirmed using FIC values.
Figure 20:
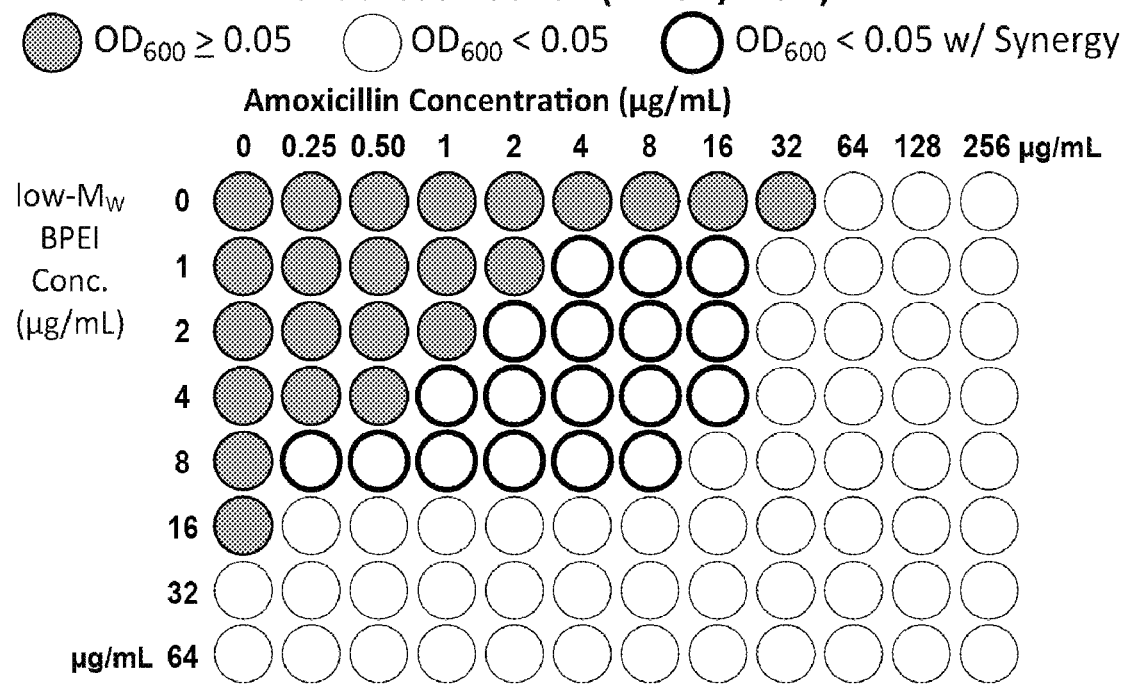
FIG. 20 is an in vitro checkerboard assay showing the effectiveness of BPEI in restoring ampicillin efficacy against MRSA. An optical density ($OD_{600}$)<0.05 was used as an indicator of growth inhibition. Synergy was confirmed using FIC values.
Figure 21:
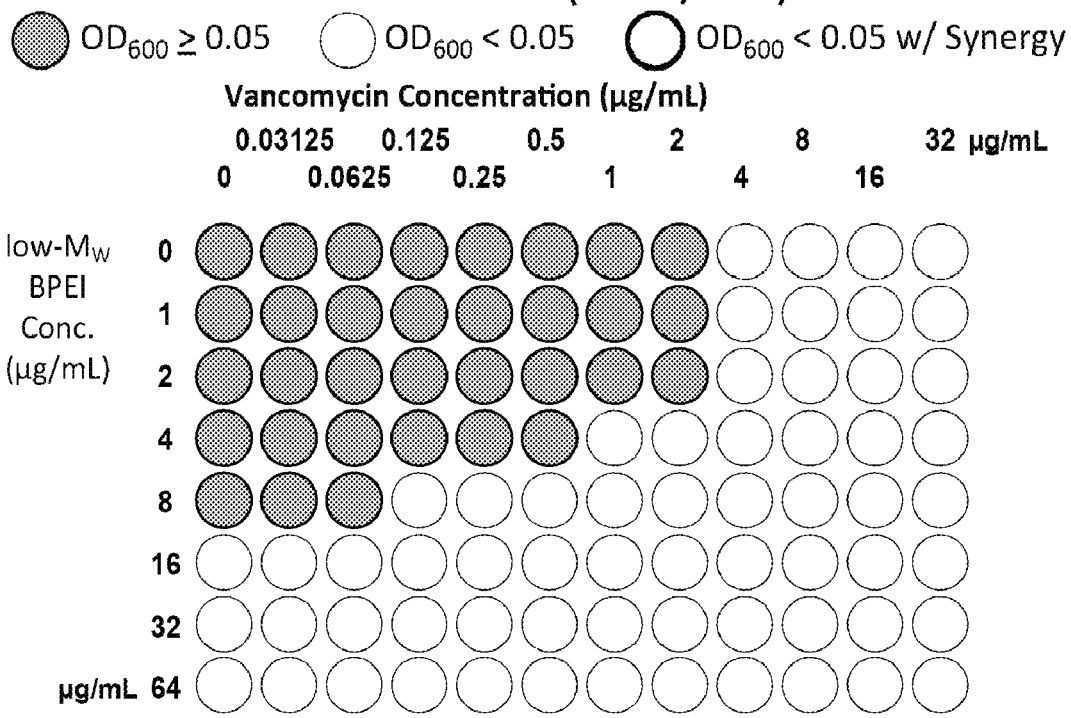
FIG. 21 is an in vitro checkerboard assay showing that Vancomycin (D) has an MIC of 4 µg/ml, denoted as intermediate resistance, but does not exhibit synergy with BPEI. Instead, the effect is additive.
Figure 22:
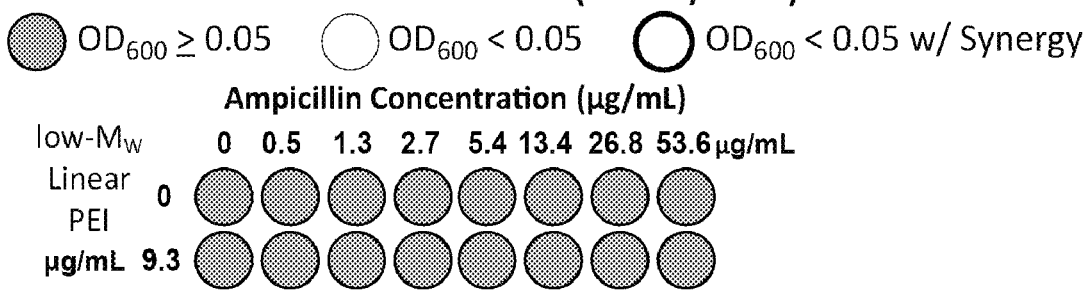
FIG. 22 shows that no potentiation of the effect of ampicillin on MRSA occurs when the linear polymer (LPEI) is used in combination with ampicillin.

Checkerboard assays were performed which confirmed anti-MRSA effectiveness of several β-lactam antibiotics, including methicillin (FIG. 18), amoxicillin (FIG. 19), and ampicillin (FIG. 20), when administered with low-$M_w$ BPEI. Without BPEI, MRSA is resistant (MIC>32 µg/mL) to methicillin, amoxicillin, and ampicillin. Increasing the concentration of low-$M_w$ BPEI decreases the methicillin MIC against the MRSA strain ATCC 700787™ that is also vancomycin-intermediate resistant (VISA). Synergy occurred with at least 6 combinations that were tested. Checkerboard data for amoxicillin (FIG. 19) and ampicillin (FIG. 20) also showed synergistic activity for certain tested combinations. Vancomycin (D) has an MIC of 4 µg/ml, denoted as intermediate resistance, but did not exhibit synergy with BPEI (FIG. 21). Instead, the effect was additive. Linear PEI (LPEI) had no effect on efficacy (FIG. 22). LPEI has 2 primary amines at the ends of the polymer and mass is similar (0.6 kDa LPEI vs. 0.5 kDa low-$M_w$ BPEI). Using a small data set, LPEI (0, 1.3, 2.7, 5.4, 13.4, 26.8, and 53.6 µg/mL) did not potentiate ampicillin (8 µg/mL).

Figure 4:
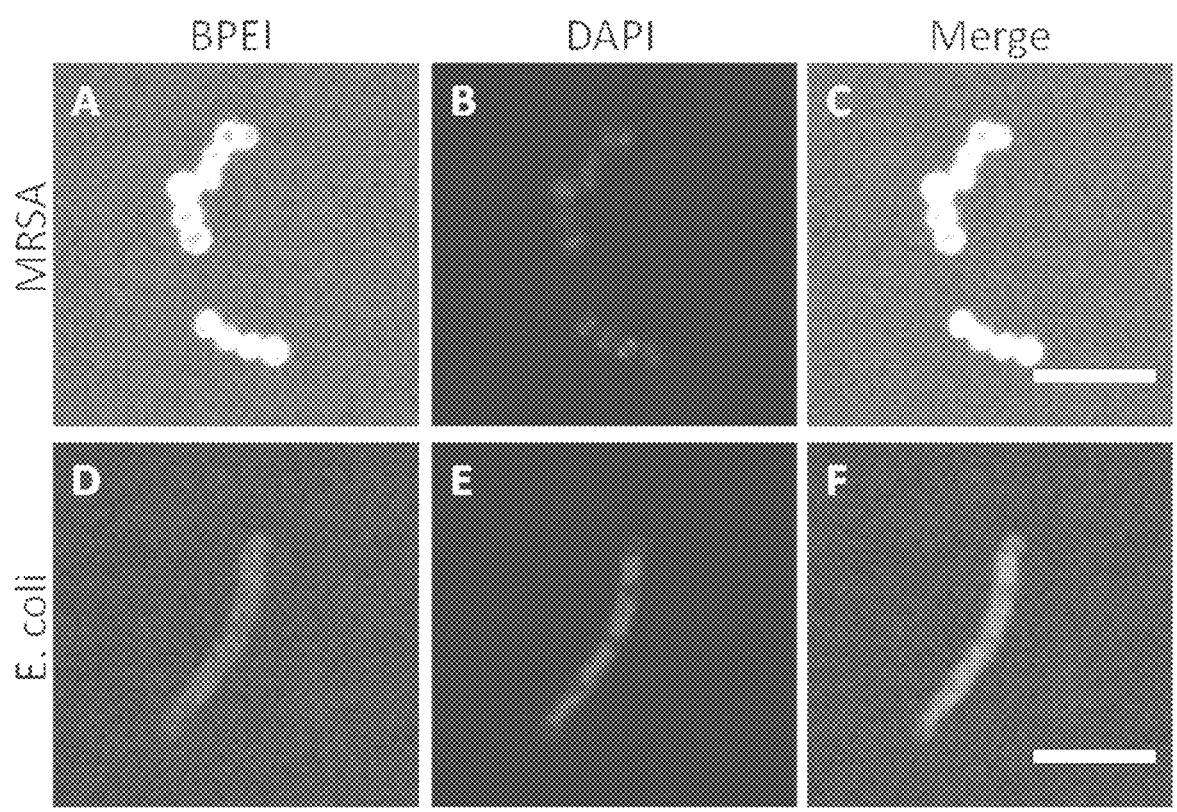
FIG. 4 show microphotographs of sections having BPEI binding to MRSA and *E. coli*. Paraformaldehyde-fixed MRSA, imaged by Laser Scanning Confocal Microscopy (LSCM), stained with BPEI-AlexaFluor 488 (A) and 4',6-diamidino-2-phenylindole (DAPI) (B). The merged image (C) shows BPEI binding to the cell surface but not within the cytoplasm. In contrast, PFA-fixed *E. coli* stained with BPEI-AlexaFluor 488 (D) and DAPI (E) and merged (F) shows a relatively low affinity between BPEI and *E. coli*. Scale bar=5 µm.
Figure 5:
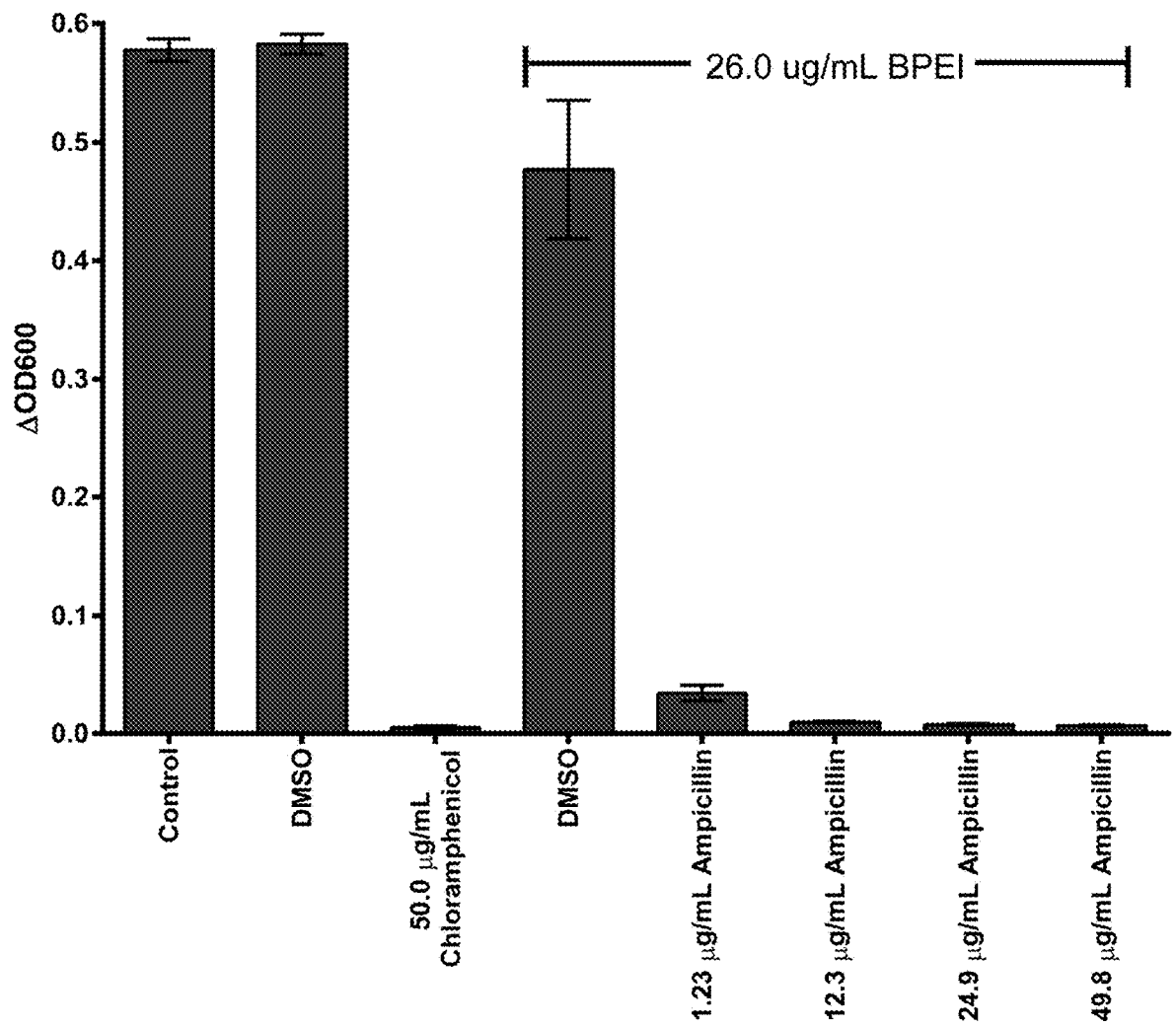
FIG. 5 shows results of an in vitro ampicillin assay against MRSA. When BPEI (26 µg/mL) is added, the MIC for ampicillin is approximately 1.2 µg/mL. The growth of MRSA was evaluated by measuring the change in $OD_{600}$ after 20 hours. Cell growth in media without additives is denoted as Control, and in media with 1% DMSO as the DMSO bars. The addition of chloramphenicol at 50 µg/mL served as a negative-growth control.
Figure 16:
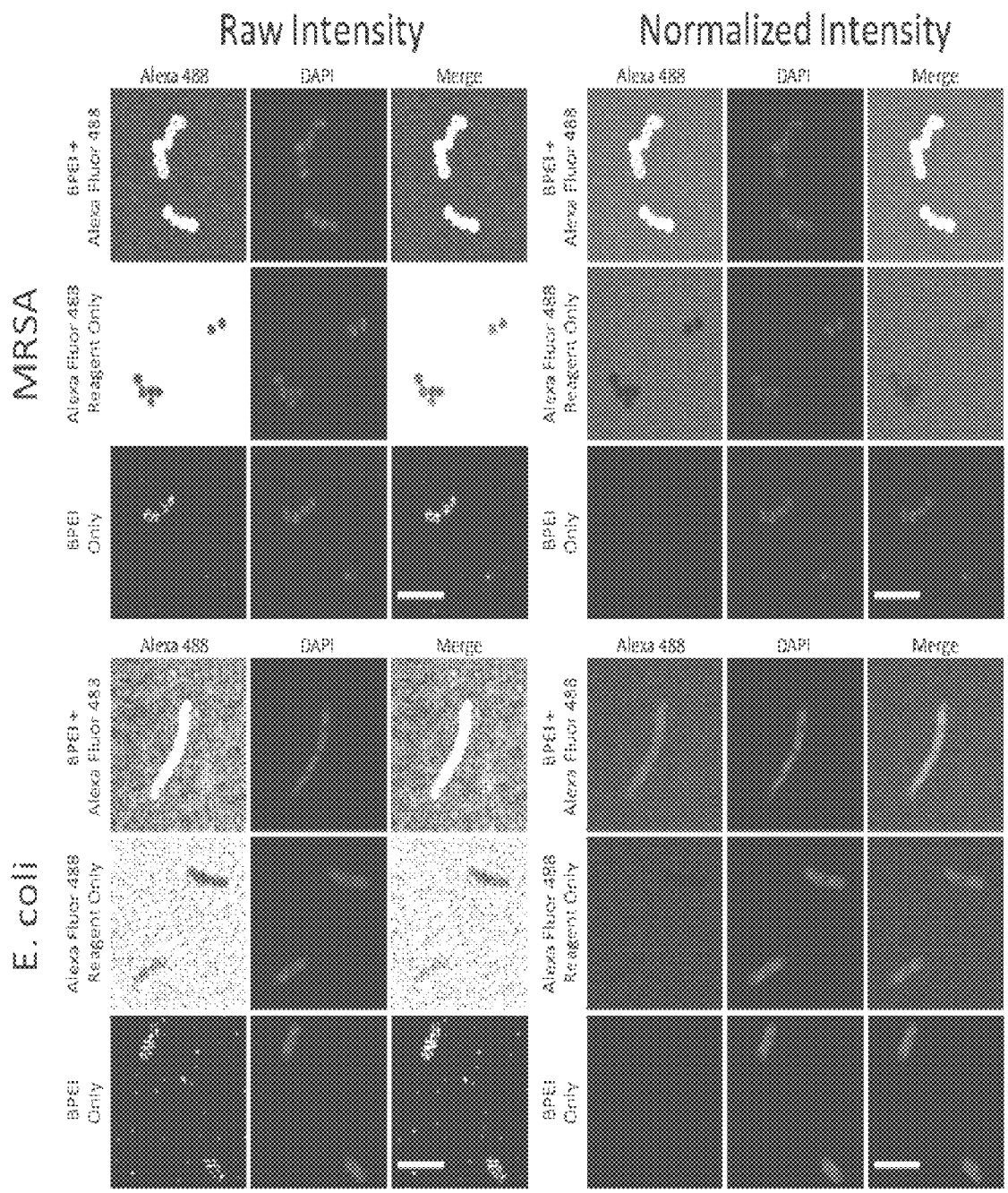
FIG. 16 shows microphotographs of sections having BPEI binding to MRSA and *E. coli*. MRSA and *E. coli* were treated with either BPEI-conjugated AlexaFluor 488 (top row), only Alexa Fluor 488 (middle row), or only BPEI (bottom row). The left column of images shows the net fluorescence intensity for each channel. The middle columns shows fluorescence intensity of cells stained with DAPI. The right column shows the merged images of both AlexaFluor 488 and DAPI staining, where the fluorescence intensities within each image were normalized relative to the intensity of fluorescence of MRSA treated with BPEI conjugated AlexaFluor 488. Scale bar=5 µm.

Without wishing to be bound by theory, data presented herein indicate that BPEI interacts or interferes with with PBP2a. This would prevent the enzyme from functioning properly while allowing the β-lactam to disable PBP1 and PBP3. If true, BPEI's interaction with MRSA should be confined to the cell wall. By conjugating BPEI to a fluorescent marker, Alexa-Fluor 488, we were able to visualize BPEI localization in bacterial cultures using LSCM. Individual transverse optical sections clearly show BPEI interaction with the MRSA cell wall region (FIG. 4A). Using DAPI, a DNA-binding fluorescent dye, as a marker for the cytoplasm within the cells (FIG. 4B) the merged image (FIG. 4C) confirms that BPEI was not detected within the cytoplasm, verifying that BPEI does not traverse the lipid bilayer membrane. Similar optical sections of *E. coli* cells treated with BPEI-conjugated Alexa-Fluor 488 revealed minimal fluorescence intensity within the cell envelope, indicating a weaker interaction between the *E. coli* cell envelope and BPEI (FIGS. 4D-F). This may explain the absence of antibiotic potentiation against *E. coli* in our present study. Additional LSCM images of the samples are provided as supplemental data (FIG. 16).

The microscopy data, showing BPEI located in the cell wall region and not the cytoplasm, indicates that the observed antibiotic potentiation against MRSA is caused by an interaction of BPEI with some component of the bacterial cell wall. One major component of the Gram-positive cell wall is wall teichoic acid (WTA), a phosphodiester polymer whose anionic phosphate groups have been shown to interact strongly with metal cations. BPEI, with its polycationic properties, has the potential for very strong electrostatic interactions with the polyanionic WTA molecules, for example via the primary amines of BPEI, and the phosphate groups of WTA. This interaction can be observed using nuclear magnetic resonance (NMR) studies of mixed BPEI-teichoic acid solutions when compared to NMR spectra of teichoic acid alone. The 1-D $^{31}$P spectra (FIG. 17A-B) show significant changes after mixing WTA with low-$M_w$ BPEI. WTA is a phosphodiester polymer with heterogeneous arrangement of N-acetylglucosamine (NAG), D-alanine, and hydroxyl groups. This creates variations in conformation of the poly(ribitol) backbone and differences in the phosphate conformations that generate distinct $^{31}$P NMR peaks. In the presence of low-$M_w$ BPEI, the $^{31}$P NMR peak at 1.3 ppm is very intense, demonstrating that a large fraction of the phosphates have similar conformations. However, signals near 4 ppm are produced by phosphates in a deshielded environment. The downfield shift arises from a loss of electron density around the phosphorous nucleus, an effect that could be caused by a hydrogen bond between the phosphate oxygen and a BPEI amine group. The addition of BPEI also increases the intensity of cross peaks in the $^1H\{^{31}P\}$ HMBC (heteronuclear multiple bond coupling) NMR data (FIG. 17C-D). This experiment relies on strong through-bond coupling between the $^1H$ and $^{31}P$ nuclei. For flexible molecules, internal motion and dynamics causes relaxation of NMR signals and thus the $^1H\{^{31}P\}$ HMBC signals are difficult to observe. When molecular motion is restricted, the signals are stronger.

Figure 15:
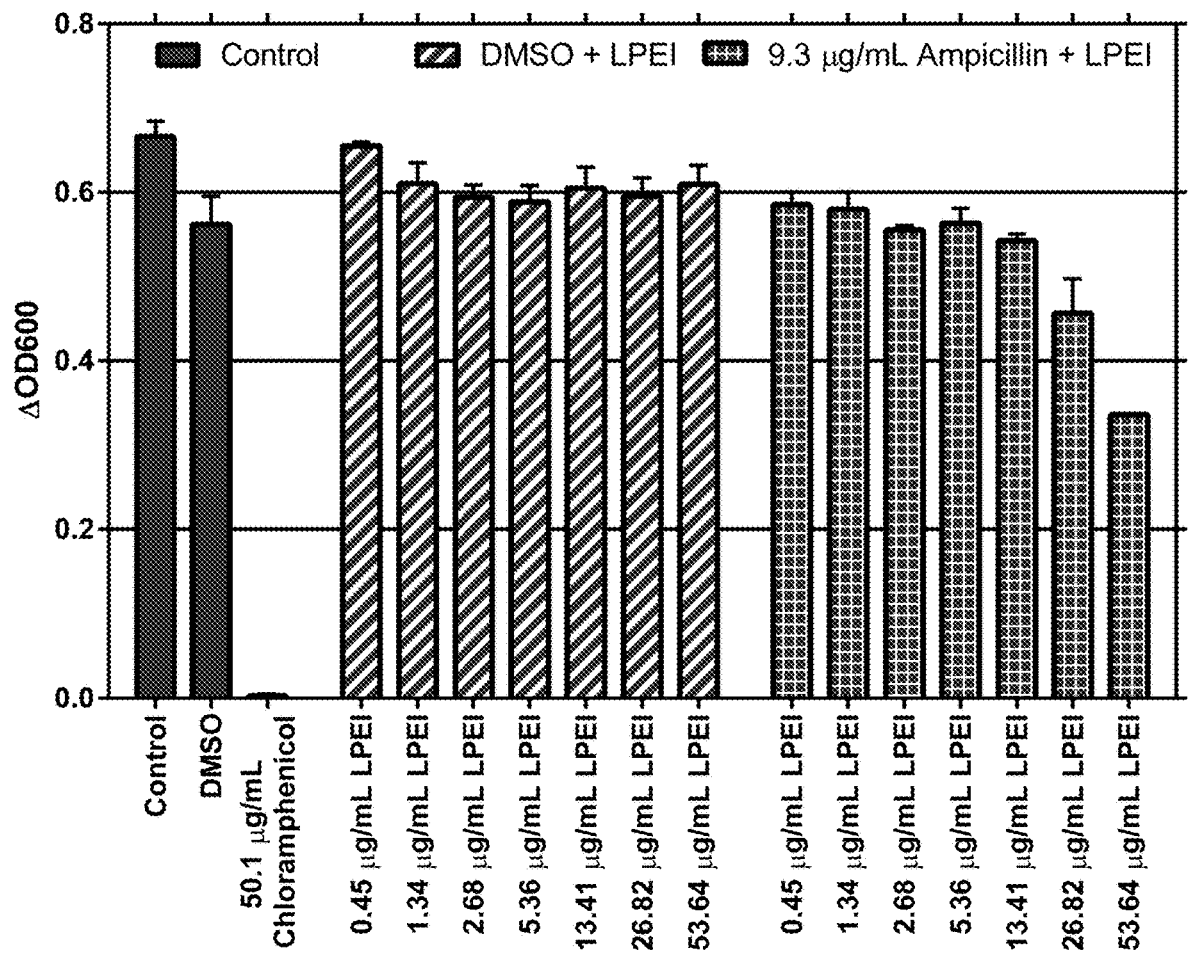
FIG. 15 shows results of an in vitro linear PEI assay against MRSA. LPEI alone does not affect the growth of MRSA through 53 µg/mL (striped columns); addition of 9.3 µg/mL ampicillin provides some synergistic effect, though not enough to inhibit MRSA growth (thatched columns). Growth of MRSA was evaluated by measuring the change in $OD_{600}$ after 20 hours. Cell growth in media (Control) or media with 1% DMSO show the increase in $OD_{600}$ (solid columns), while 50 µg/mL chloramphenicol serves as a negative control.

Without wishing to be bound by theory, phosphate:amine binding from the WTA:BPEI interactions likely occurs through electrostatic attraction between the numerous cationic primary amines of BPEI and anionic phosphate groups of WTA. If this assumption is correct linear PEI, with only the 2 primary amines at its terminal ends, should not affect ampicillin's MIC values. The 0.6 kDa form of LPEI (similar in mass to the 0.5 kDa BPEI) does not inhibit MRSA growth (FIG. 15) until its concentration is very high (54 µg/mL). Low molecular weight quaternary ammonium compounds have recently been shown to overcome resistance if the number of cationic sites is increased. Therefore, in at least certain embodiments, the optimal cationic amine polymer (BPEI) should have a relatively high number of primary amines with a low molecular weight to minimize cytotoxicity.

Figure 14:
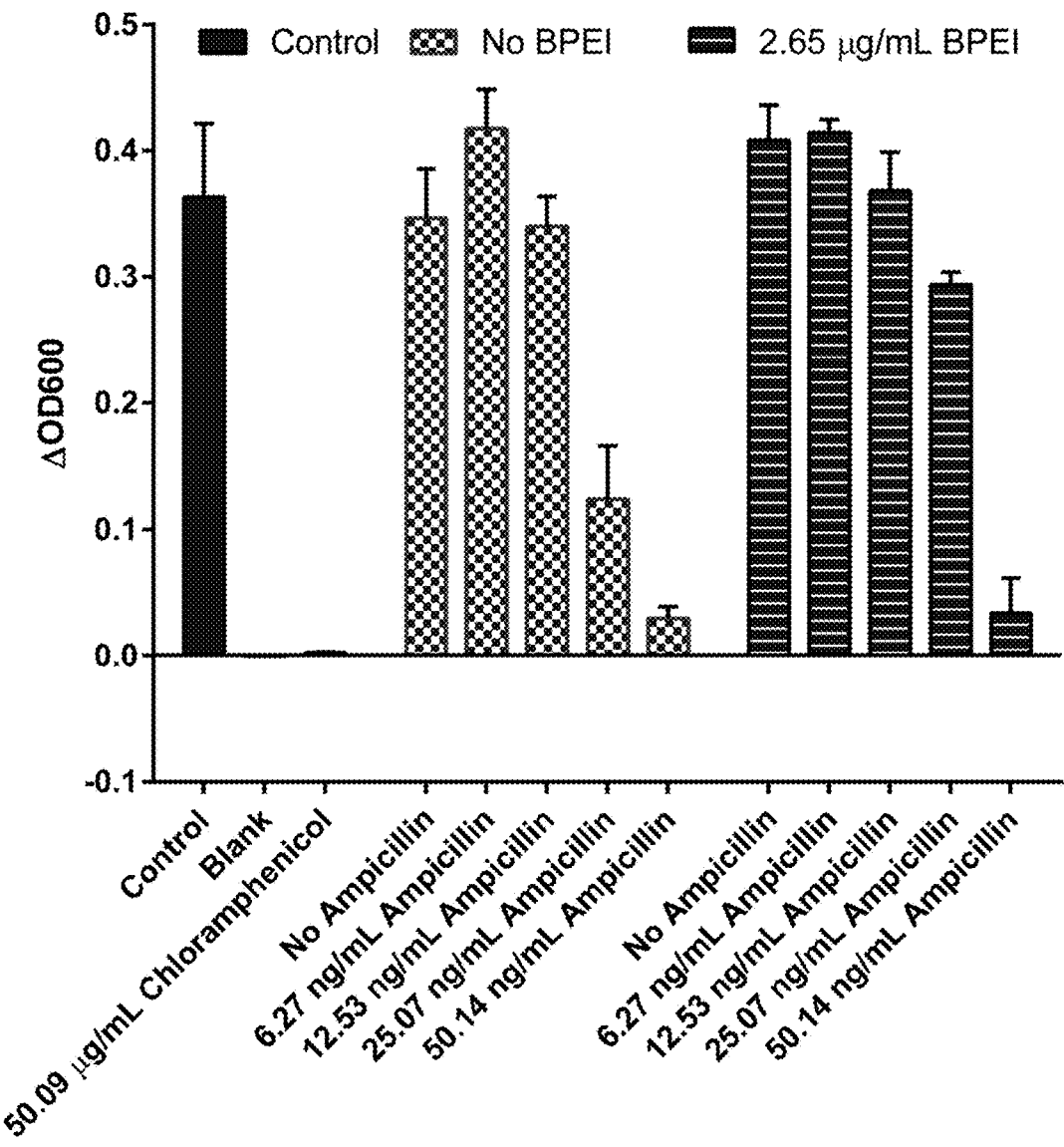
FIG. 14 shows results of an in vitro ampicillin assay against non-resistant *S. aureus*. When BPEI (2.65 µg/mL) is added, the MIC for ampicillin is approximately 50 ng/mL (striped columns), the same as for ampicillin by itself (checkered columns). Cell growth was evaluated by measuring the change in $OD_{600}$ after 20 hours. Cell growth in media without additives is denoted as Control, shown with a blank negative control and a negative growth control using 50 µg/mL chloramphenicol (solid columns).

Because low-$M_w$ BPEI binds to WTA, the cationic polymer has the ability to change WTA properties by altering molecular structure and/or creating steric bulk from the branched BPEI. This would change, interfere with, or prevent, the interaction of WTA with PBP2a and thus disable the enzyme. The same effect can be created through WTA-deficient strains of MRSA, which become re-sensitized to amoxicillin, ampicillin, methicillin, nafcillin, and ceftizoxime. An inhibitor of WTA synthesis, tunicamycin, re-sensitizes MRSA to β-lactams such as methicillin, oxacillin, cefotaxime, and several others. Inhibition of another regulatory gene, tarG, also re-sensitizes MRSA strains to traditional β-lactams like imipenem. Thus WTA, while apparently not essential to viability, is involved in β-lactam resistance. WTA helps to optimally localize PBP2a, and WTA-deficient mutants show a decreased functionality of the protein. It additionally localizes PBP4, which is essential for the highly cross-linked peptidoglycan exhibited by MRSA and for the expression of β-lactam resistance in community-acquired strains. Thus, restoration of β-lactam activity in therapeutic clinical usage could be achieved with antibiotics or other compounds that target WTA synthesis or interrupt the ability of WTA to localize PBP2a in the proper configuration required for peptidoglycan crosslinking. If this perspective is true, there should be little or no benefit when BPEI and ampicillin are used to treat non-resistant S. aureus strains that do not express PBP2a. Results in FIG. 14 show that the ampicillin MIC against methicillin-susceptible S. aureus ATCC 25923 was about 50 ng/mL. When combined with 2.65 µg/mL of BPEI, the ampicillin MIC of S. aureus ATCC 25923 was not reduced.

These data provide additional evidence for the interruption by BPEI of the ability of teichoic acid to locate PBP2/2a and 4 in the proper orientation. Further, the data for S. aureus ATCC 25923 indicate a treatment method which also prevent antibiotic resistant infections. By using a combination of BPEI and ampicillin to treat a non-resistant S. aureus infection, the emergence of β-lactam resistant strains in vivo would be slowed. This benefit would not be possible by treatment with the antibiotic alone.

Rather than developing new inhibitors which require exhaustive clinical testing, as the results indicate, we have identified FDA-approved β-lactam antibiotics that can regain their previously-lost efficacy against MRSA. Such β-lactam-BPEI combination formulations provide dramatic benefits to human health when used as a routine antibiotic therapy, eliminating, for example, S. aureus infections while simultaneously preventing the growth of ampicillin-resistant bacteria. Further, the data for S. aureus ATCC 25923 indicate a route to treat, and prevent, antibiotic resistant infections. By using a combination of BPEI and ampicillin (or other β-lactams) to treat a non-resistant S. aureus infection, the emergence of β-lactam resistant strains in vivo can be slowed. This benefit would not be possible with ampicillin alone.

Combination treatments of an antibiotic with a compound that blocks the resistance pathway have previously been shown to be a viable therapeutic strategy. For example, β-lactam antibiotics can be deactivated by bacteria that possess β-lactamases. The increasing incidence of β-lactamases has been problematic since the 1960s. Researchers discovered that amoxicillin could be co-administered with the β-lactamase inhibitor, clavulanic acid. In such combination therapies, commercialized as Augmentin®, the antibiotic is not deactivated, but rather can successfully inhibit cell wall synthesis and kill the bacterium. The amoxicillin and clavulanic acid treatment provides a compelling precedent demonstrating that combination therapies can be a successful antibacterial approach. While this approach using the Augmentin® combination effectively treats methicillin-susceptible S. aureus (MSSA) infections, MRSA bacteria will endure absent new therapies. The approach described in the present disclosure can be used to simultaneously eliminate both MSSA and MRSA infections to limit tissue damage from toxins, decreasing morbidity and mortality. Patients will not have to endure multiple treatments with an array of antibiotics to clear the infection, thereby improving quality of life. Fewer medical complications and courses of treatment will result in better patient outcomes at a lower cost to patients and providers.

Additionally, the large synergy demonstrated with chloramphenicol, while impressive, is tempered by the knowledge that chloramphenicol is rarely used clinically in humans because of adverse side effects. However, bone marrow suppression, a common side effect induced by chloramphenicol, is dose-dependent, which indicates that by lowering the MIC by using the synergistic BPEI:chloramphenicol compositions described herein can make human treatments with chloramphenicol clinically relevant once more.

The present disclosure includes in at least one embodiment an antibiotic composition comprising a β-lactam antibiotic, and a branched poly(ethylenimine) (BPEI) compound. The antibiotic composition may be effective against a bacterium which is resistant to the β-lactam antibiotic when the β-lactam antibiotic is administered alone. The β-lactam antibiotic and the BPEI compound of any of said antibiotic compositions may interact synergistically against the resistant bacterium. Any of said antibiotic compositions may have a synergistic fractional inhibitory concentration (FIC) against the resistant bacterium. Said FIC may be ≤0.5. The BPEI compound of any of said compositions may have a molecular weight in a range of 0.1 kilodalton (kDa) to 25 kDa. Any of said antibiotic compositions may comprise a pharmaceutically-acceptable carrier, vehicle, or diluent. Any of said antibiotic compositions may be effective against at least one resistant bacterium selected from the group consisting of *Enterococcus faecalis, Enterococcus faecium, Staphylococcus aureus*, methicillin-resistant *Staphylococcus aureus* (MRSA), oxacillin-resistant *Staphylococcus aureus* (ORSA), vancomycin-resistant *Staphylococcus aureus* (VRSA), a *Streptococcus pneumonia, Streptococcus mutans, Streptococcus sanguinis, Staphylococcus epidermidis, Bacillus anthracis, Bacillus cereus, Clostridium botulinum, Clostridium botulinum*, and *Listeria monocytogenes*.

The present disclosure includes in at least one embodiment a method of treating a bacterial infection in a subject, comprising administering to the subject a β-lactam antibiotic and a branched poly(ethylenimine) (BPEI) compound in amounts effective in inhibiting the bacterial infection in the subject. In the method the bacterial infection may be caused by a β-lactam antibiotic-resistant bacterium. In any of the methods the β-lactam antibiotic and the BPEI compound may be administered to the subject in sequential or simultaneous steps, or as a composition comprising both the β-lactam antibiotic and the BPEI compound. In any of said methods the β-lactam antibiotic and the BPEI compound may inhibit the bacterial infection by interacting synergistically against the bacterium causing the bacterial infection. In any of said methods the β-lactam antibiotic and the BPEI compound together may have a synergistic fractional inhibitory concentration (FIC) against the bacterium causing the bacterial infection. In said methods the FIC may be ≤0.5. In any of said methods the BPEI compound may have a molecular weight in a range of 0.1 kilodalton (kDa) to 25 kDa. In any of said methods the bacterial infection may be caused by a bacterium selected from the group consisting of *Enterococcus faecalis, Enterococcus faecium, Staphylococcus aureus*, methicillin-resistant *Staphylococcus aureus* (MRSA), oxacillin-resistant *Staphylococcus aureus* (ORSA), vancomycin-resistant *Staphylococcus aureus* (VRSA), a *Streptococcus pneumonia, Streptococcus mutans, Streptococcus sanguinis, Staphylococcus epidermidis, Bacillus anthracis, Bacillus cereus, Clostridium botulinum, Clostridium botulinum*, and *Listeria monocytogenes*. In any of said methods the β-lactam antibiotic and the BPEI compound may be administered to the subject in sequential or simultaneous steps, or as a composition comprising both the β-lactam antibiotic and the BPEI compound. In one non-limiting embodiment, the present disclosure is directed to a method for treating a bacterial infection in a subject by administering to the subject in need of such treatment an antibacterially-effective combination of a β-lactam antibiotic and a BPEI compound, wherein the antibacterially-effective combination has a fractional inhibitory concentration (FIC)≤0.5.

It will be understood from the foregoing description that various modifications and changes may be made in the various embodiments of the present disclosure without departing from their true spirit. The description provided herein is intended for purposes of illustration only and is not intended to be construed in a limiting sense. Thus, while embodiments of the present disclosure have been described herein so that aspects thereof may be more fully understood and appreciated, it is not intended that the present disclosure be limited to these particular embodiments. On the contrary, it is intended that all alternatives, modifications and equivalents are included within the scope of the inventive concepts as defined herein. Thus the examples described above, which include particular embodiments, will serve to illustrate the practice of the present disclosure, it being understood that the particulars shown are by way of example and for purposes of illustrative discussion of particular embodiments only and are presented in the cause of providing what is believed to be a useful and readily understood description of procedures as well as of the principles and conceptual aspects of the inventive concepts. Changes may be made in the formulations and compositions described herein, the methods described herein or in the steps or the sequence of steps of the methods described herein without departing from the spirit and scope of the present disclosure.

REFERENCES

1. Farha, M. A., Leung, A., Sewell, E. W., D'Elia, M. A., Allison, S. E., Ejim, L., Pereira, P. M., Pinho, M. G., Wright, G. D., and Brown, E. D. (2013) Inhibition of WTA Synthesis Blocks the Cooperative Action of PBPs and Sensitizes MRSA to β-Lactams, *ACS Chem. Biol.* 8, 226-233.
2. Hansen, M. B., Nielsen, S. E., and Berg, K. (1989) Re-examination and further development of a precise and rapid dye method for measuring cell growth/cell kill, *J Immunol Methods* 119, 203-210.
3. Khalil, H., Chen, T., Riffon, R., Wang, R., and Wang, Z. (2008) Synergy between polyethylenimine and different families of antibiotics against a resistant clinical isolate of *Pseudomonas aeruginosa, Antimicrob. Agents Chemother.* 52, 1635-1641.
4. Helander, I. M., Alakomi, H.-L., Latva-Kala, K., and Koski, P. (1997) Polyethyleneimine is an effective permeabilizer of Gram-negative bacteria, *Microbiology (Reading, U. K.)* 143, 3193-3199.
5. Thomas, K. J., and Rice, C. V. (2014) Revised model of calcium and magnesium binding to the bacterial cell wall, *Biometals* 27, 1361-1370.
6. Halye, J. L., and Rice, C. V. (2010) Cadmium Chelation by Bacterial Teichoic Acid from Solid-State Nuclear Magnetic Resonance Spectroscopy, *Biomacromolecules* 11, 333-340.
7. Wickham, Jason R., Halye, Jeffrey L., Kashtanov, Stepan, Khandogin, Jana, and Rice, Charles V. (2009) Revisiting Magnesium Chelation by Teichoic Acid with Phosphorus Solid-State NMR and Theoretical Calculations, *J Phys Chem B,* 113(7), 2177-2183.
8. Campbell, J., Singh, A. K., Maria, J. P. S., Kim, Y., Brown, S., Swoboda, J. G., Mylonakis, E., Wilkinson, B. J., and Walker, S. (2011) Synthetic Lethal Compound Combinations Reveal a Fundamental Connection between Wall Teichoic Acid and Peptidoglycan Biosyntheses in *Staphylococcus aureus, Acs Chem Biol* 6, 106-116.
9. D'Elia, M. A., Millar, K. E., Beveridge, T. J., and Brown, E. D. (2006) Wall teichoic acid polymers are dispensable for cell viability in *Bacillus subtilis, Journal of Bacteriology* 188, 8313-8316.
10. Bhaysar, A. P., Erdman, L. K., Schertzer, J. W., and Brown, E. D. (2004) Teichoic acid is an essential polymer in *Bacillus subtilis* that is functionally distinct from teichuronic acid, *Journal of Bacteriology* 186, 7865-7873.
11. Swoboda, J. G., Meredith, T. C., Campbell, J., Brown, S., Suzuki, T., Bollenbach, T., Malhowski, A. J., Kishony, R., Gilmore, M. S., and Walker, S. (2009) Discovery of a Small Molecule that Blocks Wall Teichoic Acid Biosynthesis in *Staphylococcus aureus, Acs Chem Biol* 4, 875-883.

What is claimed is:

1. A method of treating a bacterial infection in a subject in need of such treatment, comprising:
administering to the subject a penam β-lactam antibiotic selected from the group consisting of penicillin, benzathine penicillin, penicillin G, penicillin V, procaine penicillin, ampicillin, amoxicillin, methicillin, cloxacillin, dicloxacillin, flucloxacillin, nafcillin, oxacillin, temocillin, mecillinam, carbenicillin, ticarcillin, azlocillin, mezlocillin and piperacillin; and a branched poly(ethylenimine) (BPEI) compound in amounts effective in inhibiting the bacterial infection in the subject, wherein the amounts of the penam βlactam antibiotic and the BPEI compound inhibit the bacterial infection by interacting synergistically against the bacterium causing the bacterial infection, wherein the bacterium is methicillin-resistant *Staphylococcus aureus* (MRSA), and wherein the amounts of the penam β-lactam antibiotic and BPEI compound have a penam β-lactam antibiotic:BPEI compound mass ratio in a range of 100:1 to 1:100.

2. The method of claim 1, wherein the penam β-lactam antibiotic and the BPEI compound are administered to the subject in sequential or simultaneous steps, or as a composition comprising both the penam β-lactam antibiotic and the BPEI compound.

3. The method of claim 1, wherein the BPEI compound has a molecular weight in a range of 0.1 kilodalton (kDa) to 25 kDa.

4. The method of claim 1, wherein the antibiotic and BPEI are disposed in a composition comprising a pharmaceutically-acceptable carrier, vehicle, or diluent.

5. A method for treating a bacterial infection in a subject in need of such therapy, comprising administering to the subject an antibacterially-effective combination of a penam β-lactam antibiotic selected from the group consisting of penicillin, benzathine penicillin, penicillin G, penicillin V, procaine penicillin, ampicillin, amoxicillin, methicillin, cloxacillin, dicloxacillin, flucloxacillin, nafcillin, oxacillin, temocillin, mecillinam, carbenicillin, ticarcillin, azlocillin, mezlocillin and piperacillin; and a BPEI compound, wherein the antibacterially-effective combination has a fractional inhibitory concentration (FIC) ≤0.5, and wherein the penam β-lactam antibiotic and the BPEI compound of the antibacterially-effective composition interact synergistically against the bacterium, wherein the bacterium is methicillin-resistant *Staphylococcus aureus* (MRSA), and wherein the penam β-lactam antibiotic and BPEI compound in the combination comprise a penam β-lactam antibiotic:BPEI compound mass ratio in a range of 100:1 to 1:100.

6. The method of claim 5, wherein the penam β-lactam antibiotic and the BPEI compound are administered to the subject in sequential or simultaneous steps, or as a composition comprising both the penam β-lactam antibiotic and the BPEI compound.

7. The method of claim 5, wherein the BPEI compound of the antibacterially-effective combination has a molecular weight in a range of 0.1 kilodalton (kDa) to 25 kDa.

8. The method of claim 5, wherein the antibacterially-effective combination further comprises a pharmaceutically-acceptable carrier, vehicle, or diluent.

9. A method of treating a bacterial infection in a subject in need of such treatment, comprising:
administering to the subject a penam β-lactam antibiotic selected from the group consisting of penicillin, benzathine penicillin, penicillin G, penicillin V, procaine penicillin, ampicillin, amoxicillin, methicillin, cloxacillin, dicloxacillin, flucloxacillin, nafcillin, oxacillin, temocillin, mecillinam, carbenicillin, ticarcillin, azlocillin, mezlocillin and piperacillin; and a branched poly(ethylenimine) (BPEI) compound in amounts effective in inhibiting the bacterial infection in the subject, wherein the amounts of the penam or β-lactam antibiotic and the BPEI compound inhibit the bacterial infection by interacting synergistically against the bacterium causing the bacterial infection, wherein the bacterium is methicillin-resistant *Staphylococcus aureus* (MRSA), and wherein the amounts of the penam β-lactam antibiotic and BPEI compound have a penam β-lactam antibiotic:BPEI compound mass ratio in a range of 100:1 to 1:100.

10. The method of claim 9, wherein the penam β-lactam antibiotic and the BPEI compound are administered to the subject in sequential or simultaneous steps, or as a composition comprising both the penam β-lactam antibiotic and the BPEI compound.

11. The method of claim 9, wherein the BPEI compound has a molecular weight in a range of 0.1 kilodalton (kDa) to 25 kDa.

12. The method of claim 9, wherein the antibiotic and BPEI are disposed in a composition comprising a pharmaceutically-acceptable carrier, vehicle, or diluent.

13. The method of claim 1, wherein the penam β-lactam antibiotic:BPEI compound mass ratio is in a range of 50:1 to 1:50.

14. The method of claim 5, wherein the penam β-lactam antibiotic:BPEI compound mass ratio is in a range of 50:1 to 1:50.

15. The method of claim 9, wherein the penam β-lactam antibiotic:BPEI compound mass ratio is in a range of 50:1 to 1:50.

* * * * *